United States Patent
Chalupper et al.

(10) Patent No.: US 12,302,065 B2
(45) Date of Patent: May 13, 2025

(54) SYSTEMS AND METHODS FOR FREQUENCY-SPECIFIC LOCALIZATION AND SPEECH COMPREHENSION ENHANCEMENT

(71) Applicant: Advanced Bionics AG, Staefa (CH)

(72) Inventors: Josef Chalupper, Paunzhausen (DE); Smita S. Agrawal, Stevenson Ranch, CA (US)

(73) Assignee: Advanced Bionics AG, Staefa (CH)

( * ) Notice: Subject to any disclaimer, the term of this patent is extended or adjusted under 35 U.S.C. 154(b) by 916 days.

(21) Appl. No.: 17/438,298

(22) PCT Filed: Jul. 29, 2019

(86) PCT No.: PCT/US2019/043985
§ 371 (c)(1),
(2) Date: Sep. 10, 2021

(87) PCT Pub. No.: WO2020/190317
PCT Pub. Date: Sep. 24, 2020

(65) Prior Publication Data
US 2022/0191627 A1    Jun. 16, 2022

Related U.S. Application Data

(60) Provisional application No. 62/819,334, filed on Mar. 15, 2019.

(51) Int. Cl.
*H04R 25/00* (2006.01)
*A61N 1/36* (2006.01)
*A61N 1/05* (2006.01)

(52) U.S. Cl.
CPC ....... *H04R 25/505* (2013.01); *A61N 1/36038* (2017.08); *H04R 25/407* (2013.01);
(Continued)

(58) Field of Classification Search
None
See application file for complete search history.

(56) References Cited

U.S. PATENT DOCUMENTS 8,503,704 B2 * 8/2013 Francart .................. G01S 3/802
381/313
10,469,961 B2   11/2019 Chen
(Continued)

FOREIGN PATENT DOCUMENTS

WO    2009153718    12/2009

OTHER PUBLICATIONS

International Search Report and Written Opinion received in International Application No. PCT/US2019/043985.

*Primary Examiner* — Nafiz E Hoque
(74) *Attorney, Agent, or Firm* — ALG Intellectual Property, LLC

(57) ABSTRACT

An exemplary spatial enhancement system performs frequency-specific localization and speech comprehension enhancement. Specifically, the system receives an audio signal presented to a recipient of a hearing device, and generates, based on the audio signal, a first frequency signal and a second frequency signal. The first frequency signal includes a portion of the audio signal associated with a first frequency range, and the second frequency signal includes a portion of the audio signal associated with a second frequency range. Based on the first and second frequency signals, the system generates an output frequency signal that is associated with the first and second frequency ranges and that is configured for use by the hearing device in stimulating aural perception by the recipient. This generating of the output frequency signal includes processing the first frequency signal to apply a localization enhancement and processing the second frequency signal to apply a speech comprehension enhancement.

20 Claims, 12 Drawing Sheets

(52) U.S. Cl.
CPC .......... *H04R 25/552* (2013.01); *A61N 1/0541* (2013.01); *H04R 2225/43* (2013.01); *H04R 2225/53* (2013.01); *H04R 2225/67* (2013.01)

(56) References Cited

U.S. PATENT DOCUMENTS

| | | | |
|---|---|---|---|
| 2013/0208896 A1* | 8/2013 | Chatlani | H04R 5/04 381/17 |
| 2014/0277276 A1 | 9/2014 | Saoji | |
| 2016/0136425 A1* | 5/2016 | Hamacher | A61N 1/0541 607/57 |
| 2018/0332411 A1 | 11/2018 | Francart | |

* cited by examiner

| Frequency Range (Channels) | Enhancement | 0° (Front) | 90° (Cochlear Implant) | 180° (Back) | 270° (Hearing Aid) |
|---|---|---|---|---|---|
| 0 Hz – 900 Hz (1-5) | Localization | IABF / Directional mics | IABF | IABF / Directional mics | IABF |
| 900 Hz – 1.8 kHz (6-9) | Speech Comp. | Directional mics | CROS to hearing aid | Directional mics | CROS to cochlear implant |
| 1.8 kHz – 3.0 kHz (10-12) | Localization | IABF / Directional mics | IABF | IABF / Directional mics | IABF |
| 3.0 kHz – 4.5 kHz (13-15) | Speech Comp. | Directional mics | CROS to hearing aid | Directional mics | CROS to cochlear implant |
| 4.5 kHz – 8.0 kHz (16) | Localization | IABF / Directional mics | IABF | IABF / Directional mics | IABF |

Fig. 9

SYSTEMS AND METHODS FOR FREQUENCY-SPECIFIC LOCALIZATION AND SPEECH COMPREHENSION ENHANCEMENT

RELATED APPLICATIONS

The present application claims priority to U.S. Provisional Patent Application No. 62/819,334, filed Mar. 15, 2019. The contents of the provisional patent application are hereby incorporated by reference in their entirety.

BACKGROUND INFORMATION

Various types of monaural and binaural hearing systems have been developed to enable and/or enhance the ability of hearing-impaired listeners who are recipients of hearing systems to hear or otherwise perceive sound that is presented to them. For example, hearing aid systems may operate to amplify sounds (or certain frequency components of that sounds) that are difficult for recipients to perceive, cochlear implant systems may operate to directly stimulate cochlear tissue in a manner that simulates how sound would stimulate the cochlea if not for cochlear damage or irregularity, and hybrid stimulation systems may be configured to provide both electrical and acoustic stimulation, thereby serving as hybrid systems that share commonalities with both hearing aids and cochlear implants.

Certain hearing tasks can be challenging for a recipient of any type of hearing system to perform. As one example, it may be difficult to comprehend speech (e.g., of a person talking to the recipient), particularly in a noisy environment where other sounds compete with the speech content provided by the speaker. As another example, it may be difficult to localize sounds being perceived (i.e., to discern from which direction different sounds originate). Unfortunately, these types of important hearing tasks often tend to be in competition with one another as the signal processing that enhances speech comprehension typically does so at the expense of the recipient's localization ability, and vice versa.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 9 illustrates an exemplary frequency-specific enhancement plan according to principles described herein.

DETAILED DESCRIPTION

Figure 1:
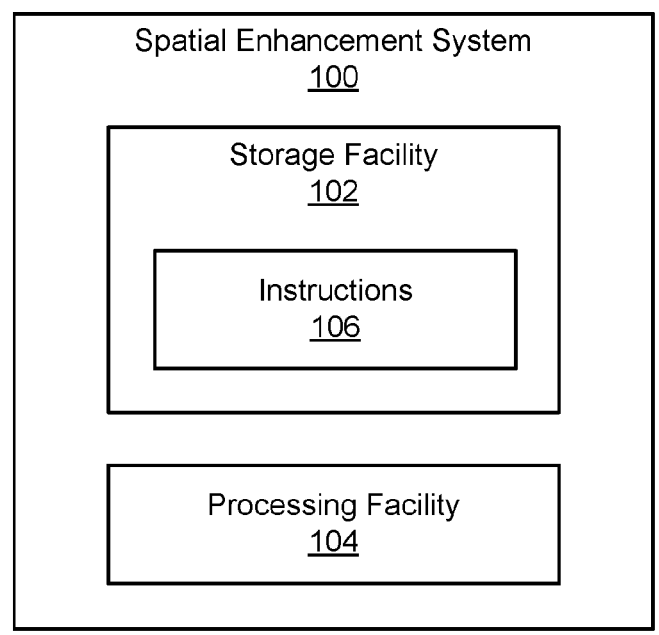
FIG. 1 illustrates an exemplary spatial enhancement system for frequency-specific localization and speech comprehension enhancement according to principles described herein.

Systems and methods for frequency-specific localization and speech comprehension enhancement are described herein. As mentioned above, it is important, but may be challenging, for recipients of various types of hearing systems (e.g., cochlear implant systems, hearing aids, hybrid stimulation systems sharing characteristics with both cochlear implant systems and hearing aids, earphones, etc.) to perform certain hearing tasks. For instance, it may be challenging to perform localization tasks involving discerning respective locations from which sounds originate, and/or to perform speech comprehension tasks involving distinguishing and understanding words spoken to the recipient.

To facilitate these tasks, various enhancements have been developed and implemented on certain hearing devices. For example, some hearing devices have implemented localization enhancements such as interaural beamforming ("IABF") operations, gain coupling operations, and/or other suitable operations for preserving and/or enhancing interaural level difference ("ILD") cues and/or interaural time difference ("ITD") cues, each of which may be used by recipients to more effectively localize sound. Various such localization enhancements will be described in more detail below, and are further described, for example, in co-pending U.S. patent application Ser. No. 16/120,203, which was filed Aug. 31, 2018, is entitled BINAURAL HEARING SYSTEMS AND METHODS FOR PRESERVING AN INTERAURAL LEVEL DIFFERENCE BETWEEN SIGNALS GENERATED FOR EACH EAR OF A USER, and is incorporated herein by reference in its entirety. Additionally, as will further be described in more detail below, speech comprehension enhancements involving use of directional microphones, dynamic directionality switching techniques, contralateral routing of signals ("CROS") techniques, and so forth, have been developed and used as speech comprehension enhancements in certain hearing devices.

Unfortunately, in previous implementations of these and other localization and speech comprehension enhancements, enhancement of a localization ability of a recipient has come at the expense of the speech comprehension of the recipient, and vice versa. As such, systems and methods for frequency-specific localization and speech comprehension enhancement described herein operate to simultaneously enhance both the localization ability and the speech comprehension of the recipient by applying the respective enhancements to distinct and/or disparate frequency ranges. For example, as will be described in more detail below, localization enhancements may be applied only to components of an audio signal within one or more particular frequency ranges (e.g., a frequency range lower than a crossover frequency) while speech comprehension enhancements may be applied only to components of the audio signal within one or more different frequency ranges (e.g., a frequency range greater than the crossover frequency).

One exemplary spatial enhancement system for frequency-specific localization and speech comprehension enhancement may include a memory storing instructions and a processor communicatively coupled to the memory and configured to execute the instructions to perform certain operations. For example, the spatial enhancement system may receive an audio signal presented to a recipient of a hearing device, and may generate a first frequency signal and a second frequency signal based on the received audio signal. The first frequency signal may include a portion of the audio signal associated with a first frequency range, and the second frequency signal may include a portion of the audio signal associated with a second frequency range. Because the second frequency range may be distinct from the first frequency range, these portions may be different (e.g., non-overlapping or only partially overlapping), and, in some examples, may be mutually exclusive. For instance, the portion of the audio signal associated with the first frequency range may include frequency components of the audio signal that are lower than a particular crossover frequency (e.g., lower than 900 Hz, lower than 1 kHz, etc.), while the portion of the audio signal associated with the second frequency range may include frequency components of the audio signal that are greater than the crossover frequency (e.g., greater than 900 Hz, greater than 1 kHz, etc.).

Based on the first and second frequency signals, the spatial enhancement system may generate an output frequency signal. For example, the output frequency signal may be associated with the first and second frequency ranges (e.g., thereby including all the frequencies lower than and greater than the crossover frequency in the example above). The output frequency signal may be configured by the hearing device for use (e.g., after additional processing) in stimulating aural perception by the recipient. In some examples, the generating of the output frequency signal may include 1) processing the first frequency signal to apply a localization enhancement, and 2) processing the second frequency signal to apply a speech comprehension enhancement (e.g., a speech comprehension enhancement that is different than the localization enhancement).

To provide a more specific example of a spatial enhancement system according to the principles described herein, an exemplary bimodal hearing system will now be described. The bimodal hearing system may include a cochlear implant device associated with a first ear of a recipient of the bimodal hearing system, and may further include a hearing aid device associated with a second ear of the recipient opposite the first ear.

The cochlear implant device may be configured to 1) receive, at the first ear, an audio signal presented to the recipient; 2) generate, based on the audio signal as received at the first ear, a first low-frequency signal and a first high-frequency signal (e.g., the first low-frequency signal including a portion of the audio signal associated with a low frequency range including audible frequencies lower than a crossover frequency, and the first high-frequency signal including a portion of the audio signal associated with a high frequency range including audible frequencies greater than the crossover frequency); and 3) generate, based on the first low-frequency and high-frequency signals, a first output frequency signal associated with the low and high frequency ranges and configured for use by the cochlear implant device in stimulating aural perception by the recipient at the first ear. Similar to the spatial enhancement system described above, the generating of the first output frequency signal by the cochlear implant device may include processing the first low-frequency signal to apply a localization enhancement, and processing the first high-frequency signal to apply a speech comprehension enhancement (e.g., a speech comprehension enhancement that is different than the localization enhancement).

In like manner, the hearing aid device in this exemplary bimodal hearing system may be configured to 1) receive, at the second ear, the audio signal presented to the recipient; 2) generate, based on the audio signal as received at the second ear, a second low-frequency signal and a second high-frequency signal (e.g., the second low-frequency signal including the portion of the audio signal associated with the low frequency range, and the second high-frequency signal including the portion of the audio signal associated with the high frequency range); and 3) generate, based on the second low-frequency and high-frequency signals, a second output frequency signal associated with the low and high frequency ranges and configured for use by the hearing aid device in stimulating aural perception by the recipient at the second ear. Similarly to the cochlear implant device, the generating of the second output frequency signal by the hearing aid device may include processing the second low-frequency signal to apply the localization enhancement, and processing the second high-frequency signal to apply the speech comprehension enhancement. It will be understood that the operations described above may be performed in any suitable sequence and/or may be performed concurrently or in parallel with one another as may serve a particular implementation.

System and methods for frequency-specific localization and speech comprehension enhancement described herein may provide various benefits and advantages. For example, unlike previous localization and speech comprehension enhancement solutions that enhance the recipient's ability to perform one type of hearing task (e.g., localization or speech comprehension) without also enhancing the recipient's ability to perform the other type of hearing task (or, in many cases, even diminishing the recipient's ability to perform the other type of hearing task), the systems and methods described herein simultaneously enhance both localization and speech comprehension. As a result, a recipient of a hearing device employing the systems and methods described herein may be able to more easily, effectively, and efficiently achieve both localization and speech comprehension hearing tasks, rather than having to enhance only one, or to enhance one at the expense of the other.

As will be described in more detail below, systems and methods described herein may be particularly beneficial to recipients of bimodal hearing systems (i.e., hearing systems including different types of hearing devices for each ear) and who may lack significant hearing ability within a certain frequency range on one side. For example, if a recipient of a bimodal hearing system has limited or no ability to perceive sounds above a particular frequency in one ear (e.g., an ear associated with a hearing aid device), but does have that ability in the other ear (e.g., an ear associated with a cochlear implant device), speech comprehension enhancements such as CROS techniques may be applied to route high frequency audio signals (e.g., speech signals) to the ear that can perceive them (thereby allowing the recipient to perceive speech originating from his or her "weak" ear) while still preserving the recipient's localization ability such that the recipient can discern that the speech signal originates from the direction of the "weak" ear, rather than the direction of the "strong" ear that is largely doing the work of perceiving and comprehending the speech. A detailed example illustrating this benefit will be described in more detail below.

Various embodiments will now be described in more detail with reference to the figures. The disclosed systems and methods may provide one or more of the benefits mentioned above and/or various additional and/or alternative benefits that will be made apparent herein.

FIG. 1 illustrates an exemplary spatial enhancement system 100 ("system 100") for frequency-specific localization and speech comprehension enhancement. System 100 may be included in, implemented by, or connected to one or more components of a hearing system that includes one or more hearing devices, such as will be described in more detail below. For example, system 100 may be implemented by a sound processor or other component of a hearing device such as a cochlear implant device, a hearing aid device, a hybrid stimulation device, or the like. As another example, system 100 may be implemented by a stand-alone computing system (e.g., a mobile device, etc.) communicatively coupled to a hearing system.

As shown in FIG. 1, system 100 may include, without limitation, a storage facility 102 and a processing facility 104 selectively and communicatively coupled to one another. Facilities 102 and 104 may each include or be implemented by one or more physical computing devices including hardware and/or software components such as processors, memories, storage drives, communication interfaces, instructions stored in memory for execution by the processors, and so forth. Although facilities 102 and 104 are shown to be separate facilities in FIG. 1, facilities 102 and 104 may be combined into fewer facilities, such as into a single facility, or divided into more facilities as may serve a particular implementation. In some examples, each of facilities 102 and 104 may be distributed between multiple devices as may serve a particular implementation.

Storage facility 102 may maintain (e.g., store) executable data used by processing facility 104 to perform any of the functionality described herein. For example, storage facility 102 may store instructions 106 that may be executed by processing facility 104 to perform one or more of the operations described herein. Instructions 106 may be implemented by any suitable application, software, code, and/or other executable data instance. Storage facility 102 may also maintain any data received, generated, managed, used, and/or transmitted by processing facility 104.

Processing facility 104 may be configured to perform (e.g., execute instructions 106 stored in storage facility 102 to perform) various operations associated with performing frequency-specific localization and speech comprehension enhancement. For example, processing facility 104 may be configured to receive an audio signal presented to a recipient of a hearing device (e.g., a hearing device that implements, is included within, or is communicatively coupled with system 100), and to generate a first frequency signal and a second frequency signal based on the audio signal. The first frequency signal may include a portion (e.g., one or more frequency components) of the audio signal associated with a first frequency range and the second frequency signal may include a portion of the audio signal associated with a second frequency range distinct from the first frequency range. For example, as will be described in relation to certain specific examples below, processing facility 104 may include hardware and/or software configured to transform the audio signal from the time domain into the frequency domain (e.g., by way of a fast Fourier transform ("FFT") technique, or the like), and the first frequency signal may include certain frequency components of the frequency-domain output of the transform while the second frequency signal includes different frequency components of the frequency-domain output (e.g., the remainder of the components output by the transform, components in a different frequency range than those components included in the first frequency signal, etc.).

Based on the first and second frequency signals, processing facility 104 may generate an output frequency signal. In some examples, the output frequency signal may be associated with both the first and second frequency ranges (e.g., to recombine the signals to again cover the entire frequency range of the original audio signal). Additionally, the output frequency signal may be configured for use by the hearing device in stimulating aural perception by the recipient. For example, after additional processing (e.g., mixing with other signals, transforming from the frequency domain back to the time domain, calibrating, balancing, mapping, amplifying, transmitting, and/or other suitable data processes), the output frequency signal may be used by the hearing device to direct acoustic and/or electrical stimulation to be applied to the recipient as may be appropriate depending on the type of hearing device being used.

In certain examples, processing facility 104 may generate the output frequency signal by performing operations configured to implement frequency-specific localization and speech comprehension enhancement in the ways described herein. For instance, processing facility 104 may process the first frequency signal to apply a localization enhancement and may process the second frequency signal to apply a speech comprehension enhancement. The localization enhancement may be different than the speech comprehension enhancement. For example, as will be described in more detail below, the localization enhancement may include an IABF enhancement or other ILD amplification technique, while the speech comprehension enhancement may include a CROS enhancement, a directional microphone tracking enhancement, or the like.

Certain implementations of system 100 may be specifically configured to perform frequency-specific localization and speech comprehension enhancement in real time (e.g., as the audio signal is being originated and received in real time). Accordingly, any of the operations described above to be performed by processing facility 104 may be performed immediately and without undue delay, such that aural stimulation (e.g., acoustic stimulation in the case of a hearing aid device or hybrid stimulation device, electrical stimulation in the case of a cochlear implant device or hybrid stimulation device, etc.) is applied to the recipient in a manner that is perceived by the recipient to be instantaneous as the audio signal is incoming (e.g., as another person is speaking to the recipient, etc.).

These and other functions that may be performed by processing facility 104 are described herein. In the description that follows, any references to functions performed by system 100 may be understood to be performed by processing facility 104 based on instructions 106 stored in storage facility 102.

Figure 2A:
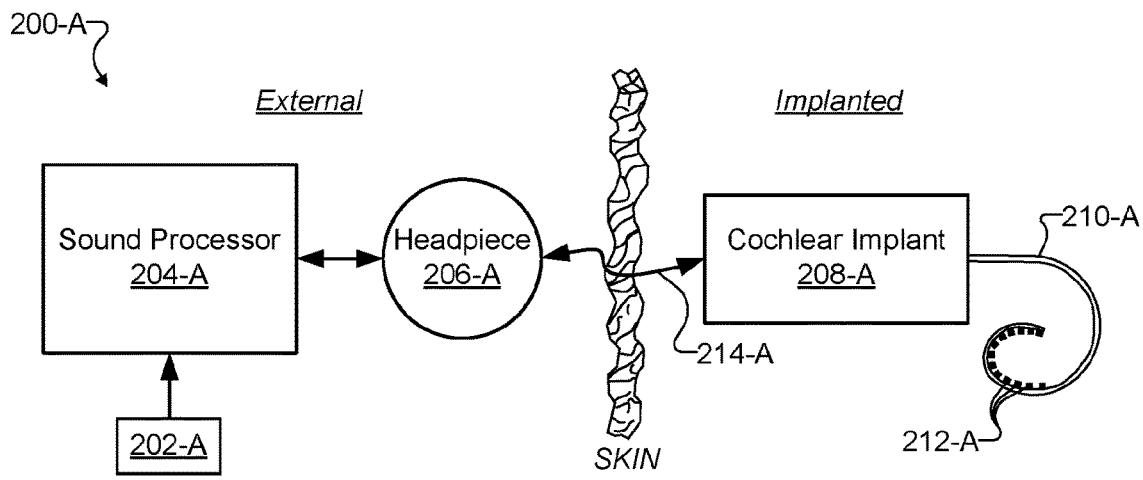
FIGS. 2A-2C illustrate exemplary components of a variety of different types of exemplary hearing devices configured to implement frequency-specific localization and speech comprehension enhancement according to principles described herein.
Figure 2B:
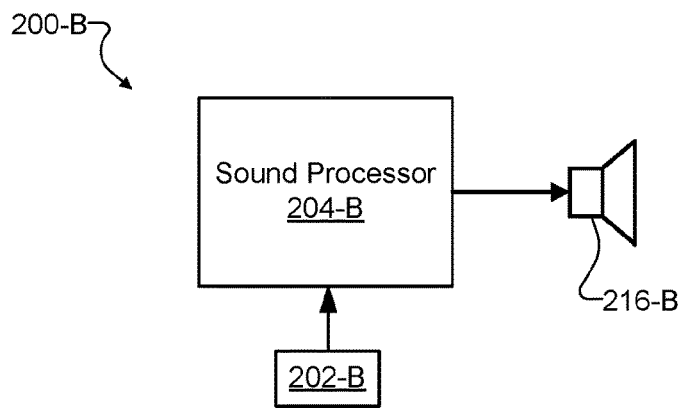
Figure 2C:
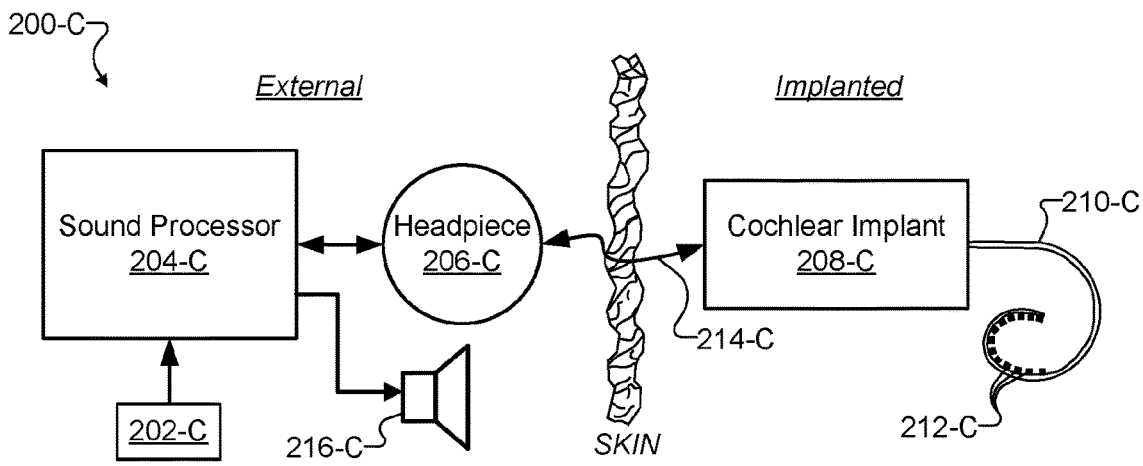

FIGS. 2A through 2C illustrate exemplary components of a variety of different types of exemplary hearing devices configured to implement frequency-specific localization and speech comprehension enhancement according to principles described herein. Specifically, FIG. 2A depicts exemplary components of a cochlear implant device 200-A, FIG. 2B depicts exemplary components of a hearing aid device 200-B, and FIG. 2C depicts exemplary components of a hybrid stimulation device 200-C. As used herein, a "hearing device 200" may refer, in accordance with the context in which the term is used, to any or all of devices 200-A, 200-B, and 200-C, or to another hearing device that is not explicitly illustrated herein but that may serve a particular implementation (e.g., earphones, etc.). As shown in FIGS. 2A through 2C, analogous components are labeled using like numbers, but using letters (i.e., 'A', 'B', or 'C') that correspond to the specific hearing device. For example, each of the hearing devices 200 includes a respective audio input device 202 that performs a similar function, but that are differentiated using respective letters (i.e., audio input device 202-A for hearing system 200-A, audio input device 202-B for hearing system 200-B, and audio input device 202-C for hearing system 200-C). In the description below with respect to other FIGS., components with the same numbers (e.g., an "audio input device 202") but without specific letters will be understood to represent the indicated components for any suitable type of hearing device (e.g., any of audio input devices 202-A through 202-C). Each of hearing devices 200 will now be described in more detail.

FIG. 2A depicts cochlear implant device 200-A. As shown, cochlear implant device 200-A may include various components configured to be located external to the recipient of the cochlear implant device including, but not limited to, an audio input device 202-A, a sound processor 204-A, and a headpiece 206-A. Cochlear implant device 200-A may further include various components configured to be implanted within the recipient including, but not limited to, a cochlear implant 208-A (also referred to as an implantable cochlear stimulator) and a lead 210-A (also referred to as an intracochlear electrode array) with a plurality of electrodes 212-A disposed thereon. As will be described in more detail below, additional or alternative components may be included within cochlear implant device 200-A as may serve a particular implementation.

Audio input device 202-A may be configured to detect audio signals presented to the recipient. Audio input device 202-A may be implemented in any suitable manner. For example, audio input device 202-A may include a microphone such as a T-MIC™ microphone from Advanced Bionics. Such a microphone may be associated with a particular ear of the recipient such as by being located in a vicinity of the particular ear (e.g., within the concha of the ear near the entrance to the ear canal) or held within the concha of the ear near the entrance of the ear canal by a boom or stalk that is attached to an ear hook configured to be selectively attached to sound processor 204-A. In other examples, audio input device 202-A may be implemented by one or more microphones disposed within headpiece 206-A, one or more microphones disposed within sound processor 204-A, one or more omnidirectional microphones with substantially omnidirectional polar patterns, one or more directional microphones, one or more beam-forming microphones (e.g., omnidirectional microphones combined to generate a front-facing cardioid polar pattern), and/or any other suitable microphone or microphones as may serve a particular implementation. Additionally or alternatively, audio input device 202-A may be implemented as an audio source other than the microphones described above. For instance, audio input device 202-A may be implemented as a telecoil, as a digital device (e.g., a Bluetooth device, an FM device, a mobile device, a media player device, etc.) providing prerecorded audio or audio received from an audio source such as a digital media service, as a remote microphone that captures and transmits an audio input signal, and/or as any other suitable source of an audio signal that may be presented to the recipient in a particular implementation.

In some examples, audio input device 202-A may "receive" an audio signal by detecting an acoustic signal and generating the audio signal by converting the acoustic energy in the acoustic signal to electrical energy in an electrical signal (e.g., a time-domain audio signal). In certain examples, the audio signal received (e.g., detected and generated) by audio input device 202-A may further be filtered (e.g., to reduce noise, to emphasize or deemphasize certain frequencies in accordance with the hearing of a particular recipient, etc.), beamformed (e.g., to "aim" a polar pattern of the microphone in a particular direction such as in front of the recipient), gain adjusted (e.g., to amplify or attenuate the signal in preparation for processing by sound processor 204), and/or otherwise pre-processed by other components included within the audio input device 202-A as may serve a particular implementation.

Sound processor 204-A (i.e., one or more computing components included within sound processor 204-A) may be configured to direct cochlear implant 208-A to generate and apply electrical stimulation (also referred to herein as "stimulation current") representative of one or more audio signals (e.g., one or more audio signals received by audio input device 202-A) to one or more stimulation sites associated with an auditory pathway (e.g., the auditory nerve) of the recipient. Exemplary stimulation sites include, but are not limited to, one or more locations within the cochlea, the cochlear nucleus, the inferior colliculus, and/or any other nuclei in the auditory pathway. While, for the sake of simplicity, electrical stimulation will be described herein as being applied to one or both of the cochleae of a recipient, it will be understood that stimulation current may also be applied to other suitable nuclei in the auditory pathway. To this end, sound processor 204-A may process the one or more audio signals in accordance with a selected sound processing strategy or program to generate appropriate stimulation parameters for controlling cochlear implant 208-A. Sound processor 204-A may include or be implemented by a behind-the-ear ("BTE") unit, a body worn device, and/or any other sound processing unit as may serve a particular implementation.

In some examples, sound processor 204-A may wirelessly transmit stimulation parameters (e.g., in the form of data words included in a forward telemetry sequence) and/or power signals to cochlear implant 208-A by way of a wireless communication link 214-A between headpiece 206-A and cochlear implant 208-A. It will be understood that communication link 214-A may include a bidirectional communication link and/or one or more dedicated unidirectional communication links. In the same or other examples, sound processor 204-A may transmit (e.g., wirelessly transmit) information such as an audio signal detected by audio input device 202-A to another sound processor (e.g., a sound processor associated with another ear of the recipient). For example, as will be described in more detail below, the information may be transmitted to the other sound processor by way of a wireless audio transmission link (not explicitly shown in FIG. 1).

Headpiece 206-A may be communicatively coupled to sound processor 204-A and may include an external antenna (e.g., a coil and/or one or more wireless communication components) configured to facilitate selective wireless coupling of sound processor 204-A to cochlear implant 208-A. Headpiece 206-A may additionally or alternatively be used to selectively and wirelessly couple any other external device to cochlear implant 208-A. To this end, headpiece 206-A may be configured to be affixed to the recipient's head and positioned such that the external antenna housed within headpiece 206-A is communicatively coupled to a corresponding implantable antenna (which may also be implemented by a coil and/or one or more wireless communication components) included within or otherwise associated with cochlear implant 208-A. In this manner, stimulation parameters and/or power signals may be wirelessly transmitted between sound processor 204-A and cochlear implant 208-A via communication link 214-A.

Cochlear implant 208-A may include any type of implantable stimulator that may be used in association with the systems and methods described herein. For example, cochlear implant 208-A may be implemented by an implantable cochlear stimulator. In some alternative implementations, cochlear implant 208-A may include a brainstem implant and/or any other type of active implant or auditory prosthesis that may be implanted within a recipient and configured to apply stimulation to one or more stimulation sites located along an auditory pathway of a recipient.

In some examples, cochlear implant 208-A may be configured to generate electrical stimulation representative of an audio signal processed by sound processor 204-A (e.g., an audio signal detected by audio input device 202-A) in accordance with one or more stimulation parameters transmitted thereto by sound processor 204-A. Cochlear implant 208-A may be further configured to apply the electrical stimulation to one or more stimulation sites within the recipient via one or more electrodes 212-A disposed along lead 210-A (e.g., by way of one or more stimulation channels formed by electrodes 212-A). In some examples, cochlear implant 208-A may include a plurality of independent current sources each associated with a channel defined by one or more of electrodes 212-A. In this manner, different stimulation current levels may be applied to multiple stimulation sites simultaneously (also referred to as "concurrently") by way of multiple electrodes 212-A.

Figure 3:
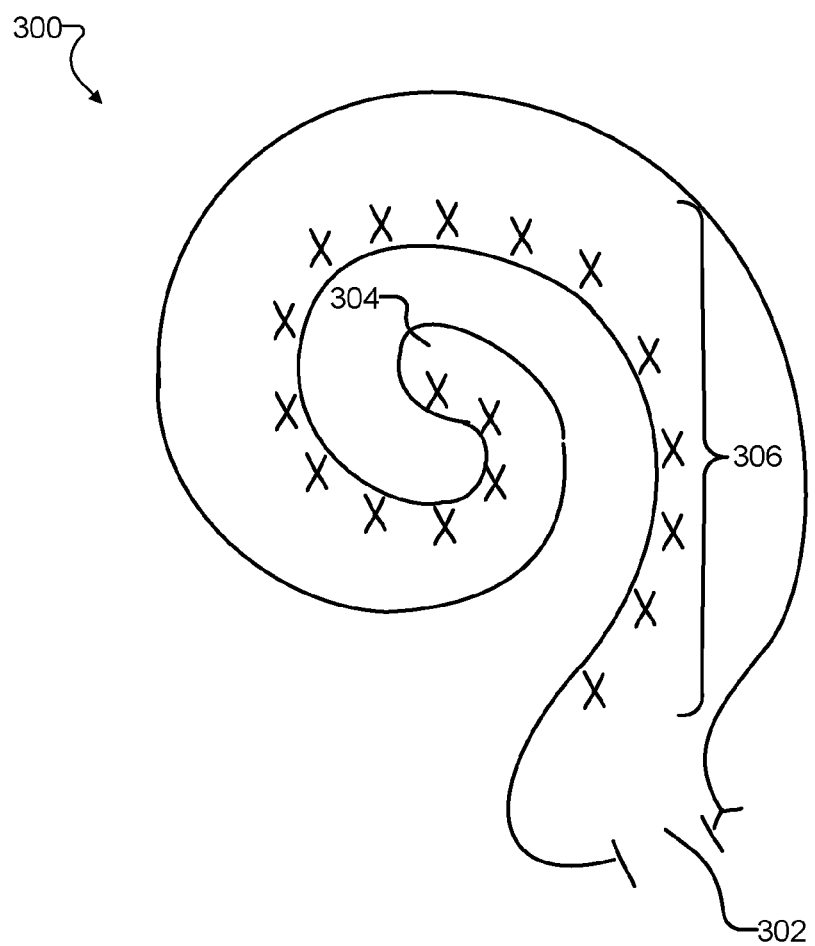
FIG. 3 illustrates a schematic structure of the human cochlea.

Prior to describing the respective hearing devices 200 of FIGS. 2B and 2C, FIG. 3 will be described to further illustrate how electrical stimulation may be applied to the recipient's cochlear tissue to induce aural perception in the recipient. FIG. 3 illustrates a schematic structure of a human cochlea 300 into which a lead (e.g., lead 210-A) may be inserted to apply electrical stimulation directly to cochlear tissue.

As shown in FIG. 3, cochlea 300 is in the shape of a spiral beginning at a base 302 and ending at an apex 304. Within cochlea 300 resides auditory nerve tissue 306, which is denoted by Xs in FIG. 3. Auditory nerve tissue 306 is organized within cochlea 300 in a tonotopic manner. That is, relatively low frequencies are encoded at or near apex 304 of cochlea 300 (referred to as an "apical region") while relatively high frequencies are encoded at or near base 302 (referred to as a "basal region"). Hence, each location along the length of cochlea 300 corresponds to a different perceived frequency. Cochlear implant device 200-A may therefore be configured to apply electrical stimulation to different locations within cochlea 300 (e.g., different locations along auditory nerve tissue 306) to provide a sensation of hearing to the recipient. For example, when lead 210-A is properly inserted into cochlea 300, each of electrodes 212-A may be located at a different cochlear depth within cochlea 300 (e.g., at a different part of auditory nerve tissue 306) such that stimulation current applied to one electrode 212-A may cause the recipient to perceive a different frequency than the same stimulation current applied to a different electrode 212-A (e.g., an electrode 212-A located at a different part of auditory nerve tissue 306 within cochlea 300).

Returning to the hearing devices of FIGS. 2A through 2C, FIG. 2B shows hearing aid device 200-B. As shown, hearing aid device 200-B includes an audio input device 202-B and a sound processor 204-B, which may each perform analogous functions, respectively, as audio input device 202-A and sound processor 204-A described above. However, instead of using a headpiece to transmit stimulation parameters to a cochlear implant configured to apply electrical stimulation directly to the recipient's cochlear tissue, as described above for cochlear implant device 200-A, hearing aid device 200-B is configured to operate under an assumption that the recipient maintains usable natural hearing ability, at least with respect to certain frequencies. Accordingly, rather than directing electrical stimulation to be applied, sound processor 204-B is configured to direct a loudspeaker 216-B to apply acoustic stimulation to the recipient, which may be perceived using the recipient's natural hearing ability. For example, hearing aid device 200-B may amplify the volume of incoming audio signals to make them easier to hear, emphasize certain frequencies, deemphasize certain frequencies, or otherwise process and present acoustic stimulation representative of incoming audio signals in any manner as may be effective in facilitating natural hearing by the recipient.

Hybrid stimulation device 200-C includes analogous elements to both cochlear implant device 200-A and hearing aid device 200-B, and may hence serve as a hybrid of these other hearing devices. Specifically, for example, hybrid stimulation device 200-C is shown to include an audio input device 202-C (similar to audio input devices 202-A and 202-B), a sound processor 204-C (similar to sound processors 204-A and 204-B), a headpiece 206-C (similar to headpiece 206-A), a cochlear implant 208-C (similar to cochlear implant 208-A), a lead 210-C with electrodes 212-C (similar to lead 210-A with electrodes 212-A), a communication link 214-C (similar to communication link 214-A), and a loudspeaker 216-C (similar to loudspeaker 216-B). Using these components, hybrid stimulation device 200-C may provide electrical stimulation directly to the cochlea of the recipient for frequencies that the recipient is unable to hear with his or her natural hearing ability, while also providing acoustic stimulation for other frequencies that the recipient is able to hear naturally.

Figure 4:
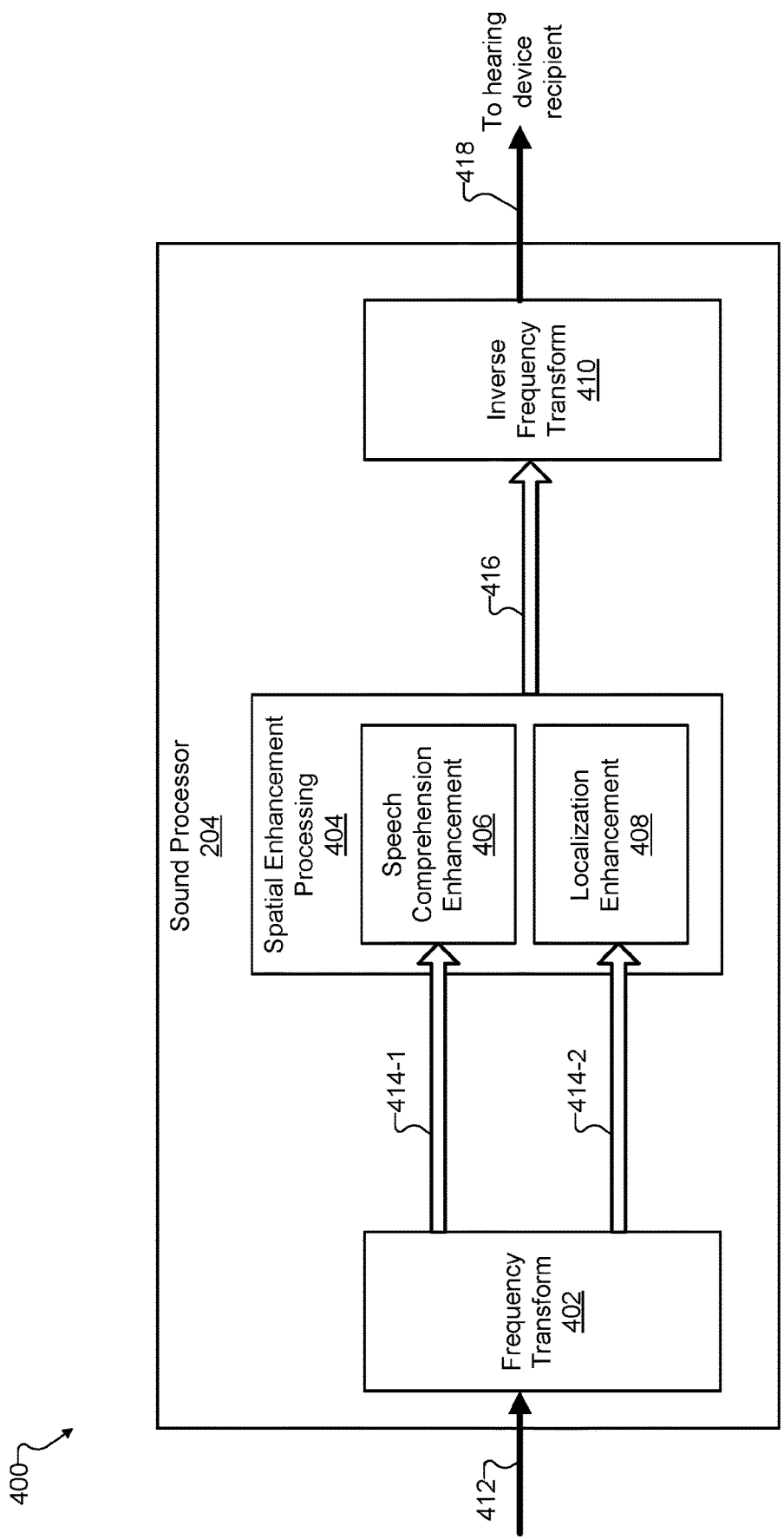
FIG. 4 illustrates exemplary components included in an exemplary sound processor of a hearing device implementing frequency-specific localization and speech comprehension enhancement according to principles described herein.

To illustrate one exemplary implementation of a spatial enhancement system integrated with one of hearing devices 200, FIG. 4 shows exemplary components included in an exemplary sound processor 204 of a hearing device 200 that implements frequency-specific localization and speech comprehension enhancement according to principles described herein. In other words, sound processor 204 in FIG. 4 illustrates exemplary details of one way that system 100 may be implemented within a hearing device 200.

As shown, sound processor 204 includes various processing units 402 through 410. More particularly, sound processor 204 includes a frequency transform unit 402, a spatial enhancement processing unit 404 that includes a speech comprehension enhancement unit 406 and a localization enhancement unit 408, and an inverse frequency transform unit 410. As shown, sound processor 204 may receive an audio signal 412, which may be used by frequency transform unit 402 to generate frequency signals 414 (e.g., frequency signals 414-1 and 414-2). Spatial enhancement processing unit 404 may generate an output frequency signal 416 based on frequency signals 414, and output frequency signal 416 may be transformed by inverse frequency transform 410 into an output audio signal 418. Each of the units and signals depicted in FIG. 4 will now be described in more detail.

Audio signal 412 may be any audio signal received by an audio input device such as any of audio input devices 202 described above. For instance, audio signal 412 may be an audio signal captured by one or more microphones that detect an acoustic signal presented to the recipient (e.g., sound waves propagating to the recipient) and convert the acoustic signal into an electronic signal such as an analog signal, a digital signal, or the like. Audio signal 412 is illustrated as a dark arrow to indicate that audio signal 412 is a time-domain signal. As such, audio signal 412 may be representative of audio data with respect to time, but may not differentiate different components of the audio based on the respective frequencies of the components. In some examples, audio signal 412 may include speech content (e.g., a person talking) or other sounds intended to be listened to and understood by the recipient (e.g., music, etc.) that originate from a particular direction. Additionally or alternatively, audio signal 412 may be representative of environmental noise and/or other sounds presented to either or both ears of the recipient.

Frequency transform unit 402 may take audio signal 412 as an input and may be configured to transform audio signal 412 into a plurality of frequency signals 414 (e.g., such as frequency signals 414-1 and 414-2, as shown in FIG. 4). While two frequency signals 414 are illustrated in FIG. 4, it will be understood that more than two frequency signals may be generated in certain examples. Specific examples having more than two frequency signals will be described in more detail below in relation to FIG. 9.

As used herein, a "frequency signal," such as one of frequency signals 414, may refer to a version of an audio signal that includes or is limited to particular frequency components of an original audio signal (e.g., audio signal 412). For instance, the frequency signal may include only those frequency components included within one or more frequency ranges that the frequency signal is said to be associated with. As one example, frequency transform unit 402 may be configured to perform a transform function (e.g., an FFT function such as a short-time FFT ("StFFT") function)) to convert a time-domain signal into a frequency-domain signal that includes complex coefficients describing the magnitude and phase of various frequency components of the signal. In this example, a frequency signal may include or represent the complex coefficients for certain of the frequency components (e.g., but, in the case of frequency signals 414, not all of the frequency components). As another example, frequency transform unit 402 may include one or more filters (e.g., low-pass filters, high-pass filters, band-pass filters, etc.) configured to filter time-domain signals covering a wide range of frequencies into filtered time-domain signals that cover narrower ranges of frequencies. In this example, frequency signals 414 may include or represent such filtered time-domain signals.

In any of these or other suitable ways, frequency transform unit 402 may divide audio input signal 412 into frequency signals 414, each of which may be associated with different frequency ranges. For example, the frequency ranges of the frequency signals may be overlapping or non-overlapping, but may be configured to not be identical. In some examples, as will be described in more detail below, the frequency ranges may together make up the entire audible frequency range. For instance, the frequency range associated with frequency signal 414-1 may include all of the audible frequencies above a particular crossover frequency and the frequency range associated with frequency signal 414-2 may include all of the audible frequencies below the crossover frequency.

In some examples, frequency transform unit 402 may convert audio signal 412 into the frequency domain using FFT operations such as StFFT operations. StFFT operations may provide particular practical advantages for converting audio signals into the frequency domain because hardware modules (e.g., dedicated StFFT chips, microprocessors or other chips that include StFFT modules, etc.) may be compact, commonly available, relatively inexpensive, and so forth.

As shown, spatial enhancement processing unit 404 may include various enhancement units (e.g., speech comprehension enhancement unit 406, localization enhancement unit 408, and/or other suitable enhancement units not explicitly shown) that are each configured to process different components of the audio signal (e.g., different frequency signals 414 that are each associated with different frequency ranges) to enhance the ability of the recipient to perform various hearing tasks. In some examples, spatial enhancement processing unit 404 may be configured to operate (e.g., using either or both of enhancement units 406 and 408) at all times or when manually activated by way of user input (e.g., user input provided by the recipient). In other examples, spatial enhancement processing unit 404 (and the enhancement units 406 and 408 included therein) may be automatically activated and/or deactivated based on various system criteria such as frequency, level, or phase characteristics of audio input signal 412 and/or frequency signals 414, or other suitable criteria as may serve a particular implementation.

Speech comprehension enhancement unit 406 may perform any suitable speech comprehension enhancement technique or algorithm as may serve a particular implementation. As used herein, speech comprehension enhancement of a signal may refer to any processing of that signal that would facilitate speech comprehension by a recipient who receives stimulation invoking aural perception based on the signal. Speech comprehension may be enhanced with respect to any subjective, objective, clinical, non-clinical, standard, non-standard, or other suitable speech comprehension criteria. For instance, speech comprehension may be enhanced when a recipient subjectively feels that he or she is able to more easily or accurately understand words spoken by others. As another example, speech comprehension may be enhanced when a recipient performs objectively better on a clinical test configured to measure listening, effort, or the like (e.g., via electroencephalogram ("EEG"), etc.).

As one example of speech comprehension enhancement, a CROS enhancement is considered in which speech sounds captured at one ear of the recipient (e.g., a "weak" ear) are routed to be presented at the other ear (e.g., a "strong" ear) to improve the recipient's ability to comprehend speech content. In a CROS speech comprehension enhancement, the hearing device may be associated with a first ear of the recipient (i.e., an ear located opposite a second ear of the recipient), and the processing of frequency signal 414-1 by speech comprehension enhancement unit 406 to apply the speech comprehension enhancement may include performing the CROS operation with respect to frequency signal 414-1 to amplify, ipsilaterally at the first ear, an aspect of the audio signal (e.g., speech content) that is received contralaterally at the second ear.

As another example, speech comprehension enhancement may include or be performed by a directional microphone tracking enhancement in which directional microphones are directed toward the speech source to emphasize (e.g., amplify) the speech while deemphasizing (e.g., attenuating) sounds originating from other directions. In some examples, directional microphones may be statically directed in a particular direction (e.g., such as toward sounds originating in front of the recipient, toward sounds originating behind the recipient, etc.). In other examples, directional microphones may be dynamically directed to track or "zoom into" sound sources even as the direction of the sound sources changes over time (e.g., as the source moves, as the recipient turn his or her head, etc.).

Speech comprehension enhancement unit 406 may process frequency signal 414-1 to apply the speech comprehension enhancement in any suitable manner. For instance, in certain examples, the processing of frequency signal 414-1 may involve performing a speech comprehension enhancement operation in accordance with a set of speech comprehension parameters. In other examples, however, the processing of frequency signal 414-1 may involve dynamically adjusting at least one speech comprehension parameter in the set of speech comprehension parameters. For example, as the speech comprehension enhancement operation is being performed in accordance with the set of speech comprehension parameters, speech comprehension enhancement unit 406 may be configured to adjust at least one speech comprehension parameter to thereby alter the manner in which the speech comprehension enhancement is applied to the signal (e.g., to alter the mixing ratio of ipsilateral and contralateral signals based on a signal-to-noise ratio, to alter the gain with which the contralateral signal is routed to the ipsilateral side, to alter the manner in which directional microphones track the speech source, etc.).

Figure 5A:
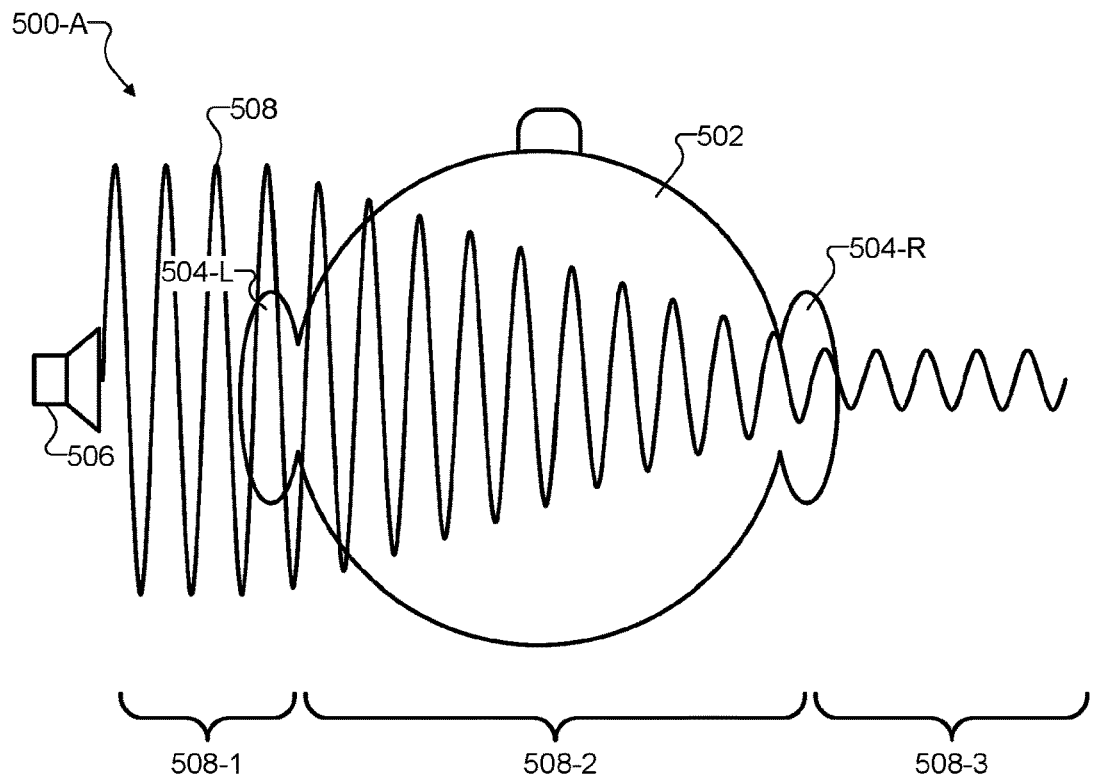
FIGS. 5A-5B illustrate exemplary principles by way of which the spatial enhancement system of FIG. 1 may implement speech comprehension enhancement according to principles described herein.
Figure 5B:
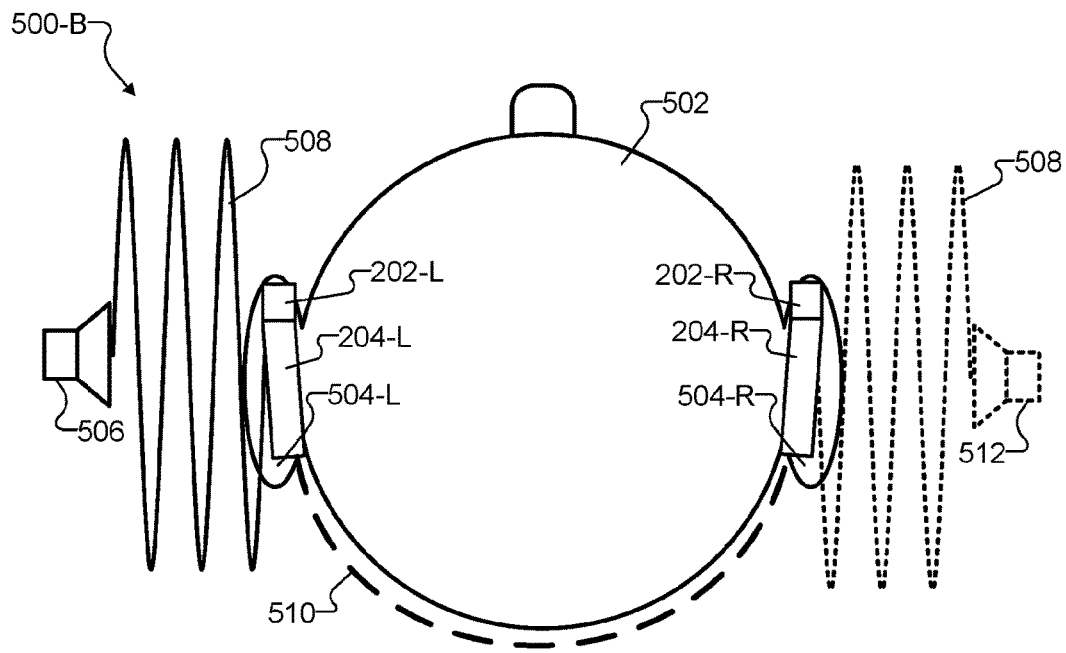

To illustrate, FIGS. 5A and 5B show exemplary principles by way of which system 100 (e.g., the implementation of system 100 shown in FIG. 4 to be integrated with sound processor 204) may implement speech comprehension enhancement. Specifically, FIGS. 5A and 5B illustrate how a CROS operation may facilitate speech comprehension by a recipient 502.

In FIG. 5A, recipient 502 is shown to have two ears 504 including a left ear 504-L and a right ear 504-R. At a location to the left of recipient 502, a sound source 506 (e.g., representative of a person who is talking to recipient 502 or another source of sound that includes speech or other nuanced sound that it is desirable for recipient 502 to comprehend) originates an acoustic signal 508 that is composed of sound waves propagating through the air toward recipient 502. The magnitude of acoustic signal 508 is illustrated in FIG. 5A by the height of acoustic signal 508. However, due to a "head-shadow effect" illustrated in FIG. 5A, that magnitude (and, with it, the volume of sound perceived by recipient 502) is not constant as acoustic signal 508 propagates toward and through or around the head of recipient 502. Specifically, a first section 508-1 of acoustic signal 508 is shown to have a relatively large magnitude that is originated by sound source 506. A second section 508-2 of acoustic signal 508 is shown to progressively drop in magnitude as acoustic energy is blocked, absorbed, reflected, or otherwise affected by the head of recipient 502 (an effect referred to as the head-shadow effect). Accordingly, by the time acoustic signal 508 reaches ear 504-R at a third section 508-3, the magnitude of acoustic signal 508 is relatively small, meaning that it will be relatively more difficult to hear and to comprehend speech based on perception at ear 504-R than based on perception at ear 504-L.

In order to enhance the ability of recipient 502 to comprehend the speech or other nuanced sounds represented by acoustic signal 508, it may be desirable for the magnitude of acoustic signal 508 to be maintained, rather than diminished, between ears 504-L and 504-R. This would be particularly true if, for example, right ear 504-R were the "stronger" of the ears of recipient 502 (e.g., if recipient 502 could only perceive relatively low frequencies at left ear 504-L but could perceive low and high frequencies at right ear 504-R).

Accordingly, as shown in FIG. 5B, a sound processor 204-L having a audio input device 202-L and located at left ear 504-L may be communicatively coupled to a sound processor 204-R having an audio input device 202-R and located at ear 504-R. Specifically, sound processors 204-L and 204-R may be communicatively coupled by way of a communication link 510, which may be implemented as any suitable type of wireless or wired link configured to exchange information between sound processors 204-L and 204-R in real time. Sound processor 204-L may be configured to perform a CROS operation in which a representation of acoustic signal 508 (or of at least an aspect of the acoustic signal, such as speech content) that is detected by audio input device 202-L may be routed directly to sound processor 204-R so as to be presented at right ear 504-R without the head-shadow attenuation illustrated in FIG. 5A. In this way, recipient 502 may perceive not only that sound source 506 is to the left of recipient 502 originating acoustic signal 508, but also that another sound source 512 (e.g., a virtual or simulated sound source that is not actually present in the physical world) originates the same acoustic signal 508 at the same magnitude as detected at left ear 504-L.

In this way, recipient 502 may be able to more easily comprehend the speech content within acoustic signal 508 because recipient 502 can hear the speech at a high magnitude at both ears 504 (e.g., at both the weak and the strong ears in the case where there is a mismatch). However, as has been mentioned, the tradeoff to this enhancement of speech comprehension is that the localization ability of recipient 502 may be compromised by this CROS operation. Specifically, in the example of FIG. 5A, recipient 502 may successfully localize sound source 506 as being to the left of recipient 502 based on the fact that the sound magnitude is greater at left ear 504-L than at right ear 504-R. This is referred to as an ILD cue and is a principal cue used by the human brain to localize sound. While the CROS operation illustrated in FIG. 5B may help with speech comprehension for the reasons described above, it is noted that the ILD cue is compromised or completely eliminated by the CROS operation, since recipient 502 may now perceive the same magnitude of acoustic signal 508 at both ears.

For this reason, system 100 may be configured to only perform the speech comprehension enhancement (e.g., the CROS operation in this example) with respect to certain frequencies, but not all audible frequencies. Specifically, returning to FIG. 4, speech comprehension enhancement unit 406 is shown to operate only on frequency signal 414-1, but not on frequency signal 414-2. For example, if frequency signal 414-1 includes relatively high frequencies that are particularly important for the nuances of speech to be comprehended, the speech comprehension enhancement may be performed only with respect to these high-frequency components of audio signal 412, thereby allowing different enhancements (e.g., a localization enhancement performed by localization enhancement unit 408) to be applied to the lower frequency components of audio signal 412 (e.g., which may be incorporated into frequency signal 412-2).

Localization enhancement unit 408 may perform any suitable localization enhancement technique or algorithm as may serve a particular implementation. As used herein, localization enhancement of a signal may refer to any processing of that signal that would facilitate localization by a recipient who receives stimulation to invoke aural perception based on the signal. For example, localization enhancement may include or be performed by way of an IABF operation with respect to frequency signal 414-2 to spatially filter frequency signal 414-2 according to an end-fire directional polar pattern (i.e., a polar pattern that is distinct from the polar pattern of frequency signal 414-2 as generated based on audio signal 412). By filtering frequency signal 414-2 according to the end-fire directional polar pattern in this way, the head-shadow effect described above may actually be emphasized and reinforced to thereby enhance the ILD cue for recipient 502 and make it easier for recipient 502 to perform localization tasks for the frequency range associated with frequency signal 414-2 (e.g., the lower frequencies in one example).

Figure 6:
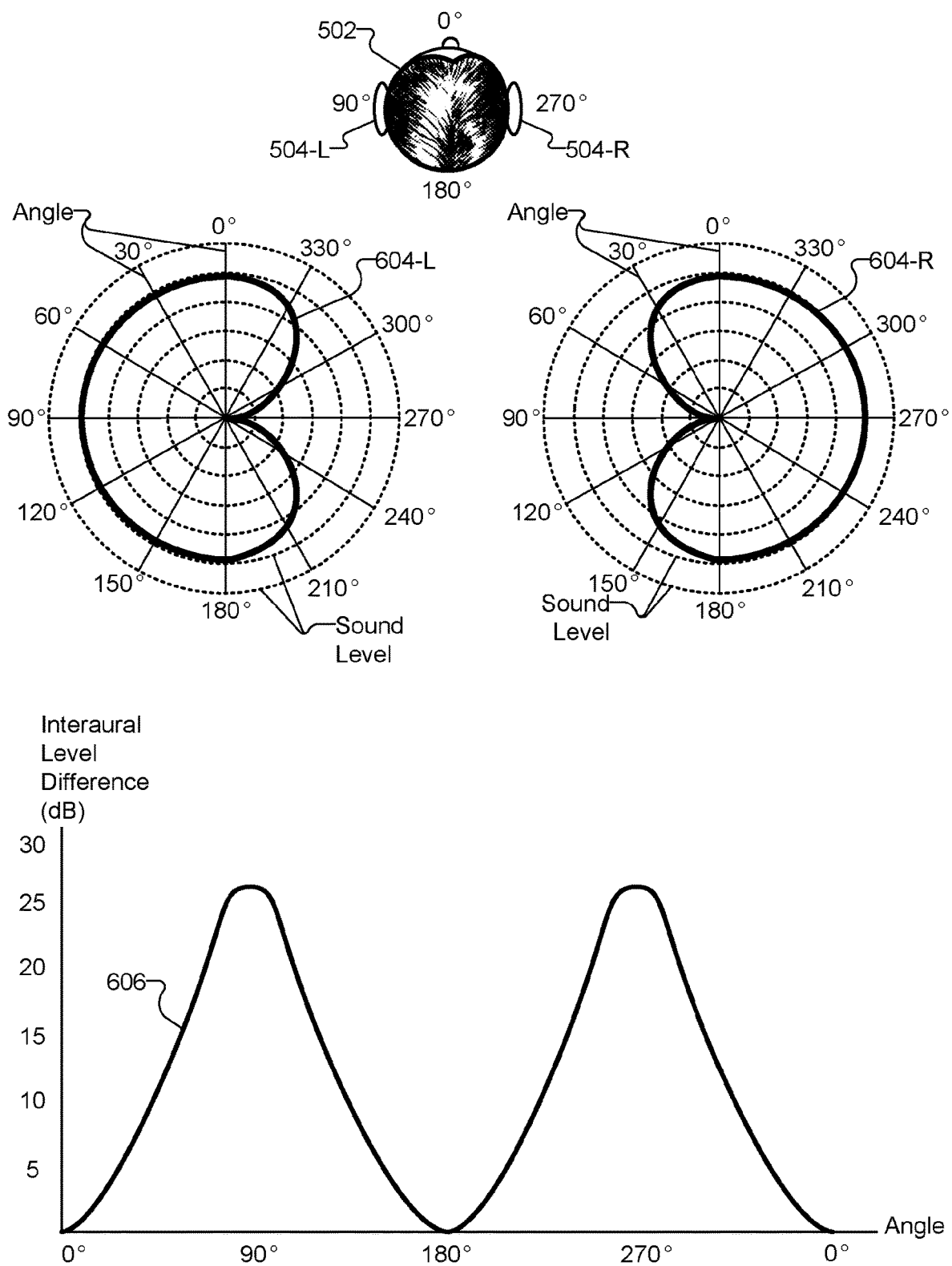
FIG. 6 illustrates exemplary principles by way of which the spatial enhancement system of FIG. 1 may implement localization enhancement according to principles described herein.

To illustrate, FIG. 6 shows exemplary principles by way of which system 100 may implement an IABF localization enhancement. As shown, a top view of recipient 502 at the top of FIG. 6 indicates certain angles with respect to recipient 502 (i.e., 0° straight in front of the recipient, 90° to the left, 180° behind, and 270° to the right). FIG. 6 also illustrates how an end-fire directional polar pattern may be implemented based on respective directional polar patterns 604 implemented at each of ears 504 (e.g., directional polar pattern 604-L for the hearing device at ear 504-L, and directional polar pattern 604-R for the hearing device at ear 504-R).

As used herein, an "end-fire directional polar pattern" may refer to a polar pattern with twin, mirror-image, outward facing lobes (as shown by directional polar patterns 604). For example, two microphones (or other suitable audio input devices 202) may be associated with mutually contralateral hearing devices 200 (e.g., including by sound processors 204-L and 204-R in FIG. 5) such as a cochlear implant and a hearing aid that are placed at each ear 504 of recipient 502. The microphones may be disposed along an axis passing from ear 504-L to ear 504-R through the head of recipient 502, and may thus form a directional audio signal according to an end-fire directional polar pattern. Specifically, by spatially filtering an audio signal detected at both microphones, system 100 may create a first lobe statically directed radially outward from the left ear in a direction perpendicular to the left ear (i.e., pointing outward at 90°), and a second lobe statically directed radially outward from the right ear in a direction perpendicular to the second ear (i.e., pointing outward from the right ear at 270°). Because the axis passes through both microphones (e.g., from ear to ear of the recipient), the direction perpendicular to the left ear of the recipient may be diametrically opposite to the direction perpendicular to the second ear of the recipient. In other words, the lobes of the end-fire directional polar pattern may point away from one another, as shown by directional polar patterns 604-L and 604-R.

To perform the IABF operation, localization enhancement unit 408 may use beamforming operations to generate an end-fire directional polar pattern from any initial polar pattern that audio signal 412 may implement when captured by audio input device 202. For example, audio signal 412 may be captured by microphones having an omnidirectional (or substantially omnidirectional) polar pattern in certain implementations, may be captured by microphones having a directional (e.g., front facing, backward facing, etc.) polar pattern in other implementations, or may be captured by other microphones or a combination of these types of microphones (or other types of audio input devices) in still other implementations. Regardless of the polar pattern of audio signal 412 (and thereby of frequency signals 414) when captured by audio input device 202, the ILD cue may be enhanced when the polar pattern is shaped to resemble the end-fire directional polar pattern illustrated by the statically opposite-facing cardioid lobes of directional polar patterns 604-L and 604-R.

As illustrated by directional polar pattern 604-L, sounds emanating directly from the left of recipient 502 (i.e., from 90°) may be detected without any attenuation at the left ear, while sounds emanating directly from the right (i.e., from 270°) may be detected with extreme attenuation or may be blocked completely. Between 90° and 270°, other sounds are associated with varying attenuation levels. For example, there is very little attenuation for any sound emanating from directly in front of recipient 502 (from 0°), directly behind recipient 502 (from 180°), or any angle relatively to the left of recipient 502 (i.e., greater than 0° and less than 180°). However, for sounds emanating from an angle in which the head shadow of recipient 502 blocks the sounds (i.e. from angles greater than 180° and less than 360°), the sound levels quickly drop off as the direct right of recipient 502 (270°) is approached, where the levels may be completely attenuated or blocked. Oppositely, as indicated by the mirror image directional polar pattern 604-R, sounds emanating directly from the right side of recipient 502 (i.e., from 270°) may be detected without any attenuation at the right ear, while sounds emanating directly from the left (i.e., from 90°) may be detected with extreme attenuation or may be blocked completely, and so forth.

To illustrate the effects of the end-fire directional polar pattern implemented by the IABF-based localization enhancement of FIG. 6, an ILD magnitude plot 606 is also shown at the bottom of FIG. 6. ILD magnitude plot 606 illustrates the magnitude (i.e., the absolute value) of the difference between the level of sounds detected at the left ear and at the right ear with respect to the angle from which the sounds emanate. Accordingly, as shown, ILD magnitude plot 606 is very low (e.g., 0 dB) around 0°, 180°, and 360° (labeled as 0° again to indicate a return to the front of the head). This is because at 0° and 180° (i.e., directly in front of recipient 502 and directly behind recipient 502), there is little or no ILD and both ears detect sounds at identical levels. Conversely, ILD magnitude plot 604 is relatively high (e.g., greater than 25 dB) around 90° and 270°. This is because at 90° and 270° (i.e., directly to the left and directly to the right of recipient 502, respectively), there is a very large ILD and one ear detects sound at a much higher level than the other ear. Put another way, ILD magnitude plot 606 illustrates how the IABF operation may emphasize, enhance, or even exaggerate the head-shadow effect and the ILD cue in order to enhance the ability of recipient 502 to perform localization tasks.

Returning to FIG. 4, other examples of localization enhancements implemented by localization enhancement unit 408 may include other ILD enhancement and magnification techniques besides the IABF operations illustrated in FIG. 6, ILD preservation techniques such as gain coupling that will be described in more detail below, ITD preservation and magnification techniques, ITD to ILD conversion techniques, monaural directivity cues (e.g., head-related transfer function ("HRTF") correction techniques, etc.) and so forth.

As with speech comprehension enhancement unit 406, localization enhancement unit 408 may process frequency signal 414-2 to apply the localization enhancement in any suitable manner. For instance, in certain examples, the processing of frequency signal 414-2 may involve performing a localization enhancement operation in accordance with a set of localization parameters. In other examples, the processing of frequency signal 414-2 may involve dynamically adjusting at least one localization parameter in the set of localization parameters. For example, as the localization enhancement operation is being performed in accordance with the set of localization parameters, localization enhancement unit 408 may be configured to adjust at least one localization parameter to thereby alter the manner in which the localization enhancement is applied to the signal (e.g., to alter the directivity or shape of the lobes of the end-fire directional polar pattern, etc.).

As the speech comprehension enhancement is applied to frequency signal 414-1 and the localization enhancement is applied to frequency signal 414-2, spatial enhancement processing unit 404 may use these processed signals to generate output frequency signal 416, which may be a frequency signal (e.g., a frequency domain signal) that as associated with (i.e., covers or corresponds to) both of the frequency ranges associated with frequency signals 414. When further processed to be presented to the recipient, the frequency components included in output frequency signal 416 may collectively facilitate the recipient in performing both speech comprehension tasks (based on frequency components of output frequency signal 416 associated with the first frequency range) and localization tasks (based on frequency components of output frequency signal 416 associated with the second frequency range).

To this end, output frequency signal 416 may be transformed from a frequency signal (e.g., a frequency domain signal, as indicated by the white arrow) into an output audio signal 418 (e.g., a time-domain signal, as indicated by the black arrow) by inverse frequency transform unit 410, which may perform an inverse FFT operation (e.g., using an inverse StFFT technique or the like) that is the inverse of operations performed by frequency transform unit 402. In some examples (e.g., if frequency signals 414 are filtered time-domain signals rather than frequency-domain signals), output frequency signal 416 may be implemented as a time-domain signal that already covers the entire frequency range. In these examples, output frequency signal 416 may serve the same purpose as output audio signal 418, and inverse frequency transform unit 410 may not be used. Output audio signal 418 may be further processed by sound processor 204 or other components of the hearing system to eventually be used in providing stimulation to the recipient. This additional processing may include mixing with other signals, calibrating, balancing, mapping, amplifying, transmitting, and/or any other operations as may serve a particular implementation.

Each of hearing devices 200-A through 200-C described above was illustrated and described in terms of a single device configured to serve a single ear (i.e., left or right) of the recipient. Additionally, the implementation of system 100 integrated with sound processor 204 illustrated in FIG. 4 illustrates only one sound processor of a single hearing device. Indeed, it will be understood that, in certain implementations, system 100 may be implemented by a monaural hearing system with only a single hearing device. For example, a single device could be customizable to be configured as a hearing aid only (e.g., with localization enhancement and directional microphones for speech comprehension enhancement), as a combined hearing aid and CROS device (e.g., with localization enhancement, directional microphones, and directional microphone tracking enhancements), or as a CROS device only (e.g., including directional microphone tracking enhancements), as may be appropriate for a particular recipient and his or her respective hearing loss profile. When an IABF localization enhancement is implemented in such a monaural hearing system, only half of the end-fire directional polar pattern (e.g., one lobe of directional polar patterns 604) may be used. When a CROS speech comprehension enhancement is implemented by such a monaural hearing system, one ear (e.g., the stronger ear) may be fitted with a hearing device, while the opposite ear may only include an audio input device (e.g., a microphone). In some situations, this may be a temporary condition, such as when a recipient loses hearing first in one ear (thus necessitating a hearing device in that ear) while retaining enough residual hearing in the opposite ear that, for some period of time, he or she can wait to get a second hearing device.

In other situations, as has also been mentioned above, any of the implementations of system 100 associated with any of the hearing devices 200 described herein may instead be associated with binaural hearing systems that include interoperating hearing devices for both left and right ears of the recipient. Specifically, for example, any of the hearing devices 200 described herein may be a first hearing device that is included in a binaural hearing system that also includes a second hearing device. Like the first hearing device, the second hearing device my include a second memory storing additional instructions and a second processor communicatively coupled to the memory and configured to execute the additional instructions to perform operations analogous to those performed by the first hearing device (e.g., receiving the audio signal, generating the first and second frequency signals, generating the output frequency signal, etc.).

Figure 7:
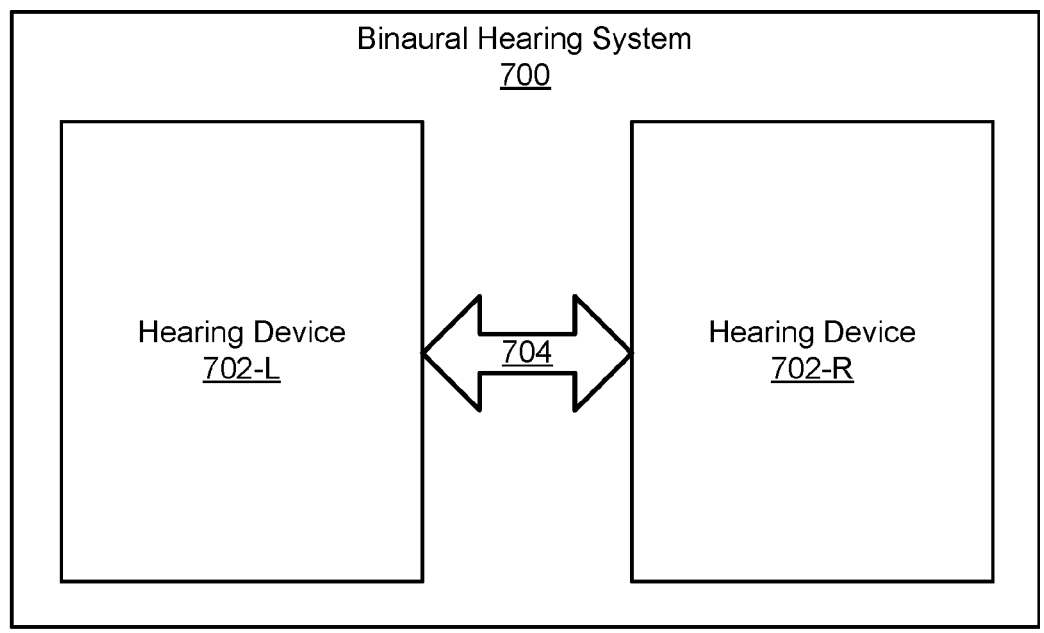
FIG. 7 illustrates an exemplary binaural hearing system that includes a respective hearing device implementing the spatial enhancement system of FIG. 1 for each ear of a recipient according to principles described herein.

To illustrate, FIG. 7 shows an exemplary binaural hearing system 700 that includes a respective hearing device 702 implementing system 100 for each ear of a recipient such as recipient 502 (i.e., hearing device 702-L for left ear 504-L of recipient 502 and hearing device 702-R for right ear 504-R of recipient 502). FIG. 7 also shows that a communication link 704 may communicatively couple hearing devices 702, thereby allowing real-time communication between hearing devices 702 within binaural hearing system 700. This real-time communication may be used to coordinate between the hearing devices and to exchange any suitable data used to implement any of the localization or speech comprehension enhancements described herein. For example, communication link 704 may represent the communication link implemented by communication link 510 in FIG. 5B to link sound processors 204-L and 204-R in the specific hearing system illustrated in that example.

In certain implementations, hearing devices 702-L and 702-R may be of the same type of hearing device. For example, binaural hearing system 700 may be implemented as a binaural cochlear implant system in which hearing devices 702-L and 702-R are each implemented as cochlear implant devices (e.g., like cochlear implant device 200-A, described above) that include respective cochlear implants and sound processors. As another example, binaural hearing system 700 may be implemented as a binaural hearing aid system in which hearing devices 702-L and 702-R are each implemented as hearing aid devices (e.g., like hearing aid device 200-B, described above). As yet another example, binaural hearing system 700 may be implemented as a binaural hybrid stimulation system in which hearing devices 702-L and 702-R are each implemented as hybrid stimulation devices (e.g., like hybrid stimulation device 200-C above) that include respective cochlear implants, sound processors, and loudspeakers.

In other implementations, hearing devices 702-L and 702-R may be of different hearing device types. As used herein, a binaural hearing system that includes two different types or modalities of hearing device will be referred to as a bimodal hearing system. Accordingly, binaural hearing system 700 may be implemented as a bimodal hearing system in which hearing device 702-L is implemented by a first type of hearing device (e.g., a cochlear implant device, a hearing aid device, a hybrid stimulation device, etc.) and hearing device 702-R is implemented by a second type of hearing device that is different from the first type of hearing device. As will be described in more detail below, one bimodal hearing system that offers particular advantages to a recipient may be a bimodal hearing system in which one of hearing devices 702 is implemented by a cochlear implant device and the other hearing device 702 is implemented by a hearing aid device.

Regardless of whether system 100 is implemented by a monaural or binaural hearing system, and regardless of what type or types of hearing devices are associated with or implement system 100, system 100 may be configured to detect and be responsive to the spatial locations from which sounds (and particularly speech sounds) originate. To this end, the processing of a frequency signal to apply a localization enhancement may involve comparing, combining, or otherwise performing signal processing on spatially filtered and unfiltered versions of the frequency signal in order to account for the spatial location of a sound source. Specifically, for example, system 100 may process 1) a first version of a frequency signal that has been spatially filtered according to an end-fire directional polar pattern, together with 2) a second version of the frequency signal that has not been spatially filtered. In this way, system 100 may explicitly identify or otherwise account for a spatial location from which an aspect (e.g., speech content) of the audio signal originates. For instance, the spatial location may be identified with respect to a pose of the recipient, or, in other words, with respect to where the recipient is located in the world and how the recipient is oriented (e.g., which direction the recipient is facing, etc.). As such, the processing of frequency signals 414-1 and 414-2 may each be performed based on the identified spatial location from which the aspect of the audio signal originates.

Figure 8:
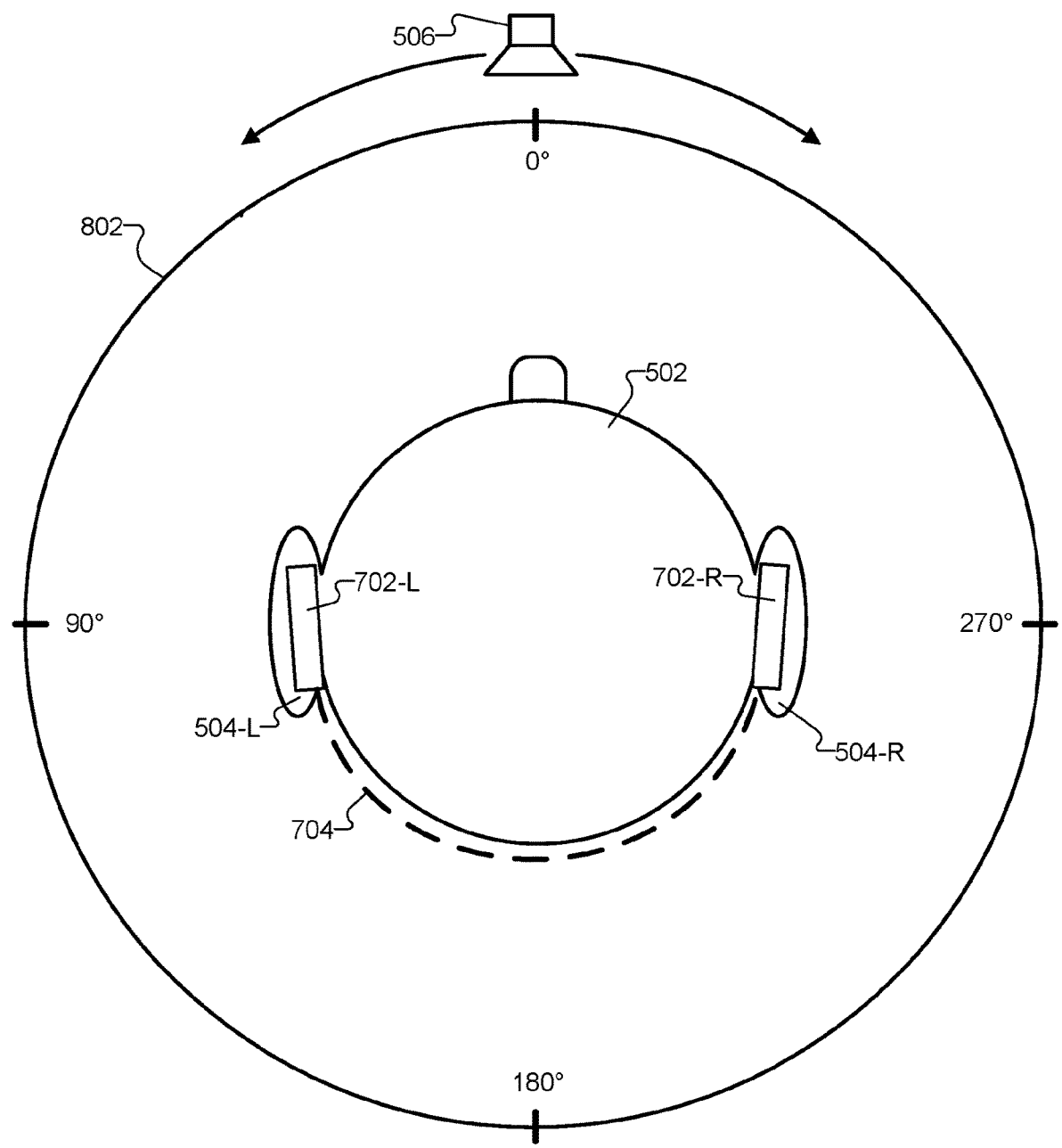
FIG. 8 illustrates exemplary spatial locations from which an audio signal may originate with respect to a pose of a recipient according to principles described herein.

To illustrate, FIG. 8 shows exemplary spatial locations from which an audio signal may originate with respect to a pose of recipient 502. Specifically, as shown, recipient 502 is shown to be facing toward the top of the page, at an angle 802 of 0°. Sound source 506 is also shown to presently be located at an angle 802 of 0°, although, as indicated by arrows next to sound source 506, it will be understood that the angle at which sound source 506 is located with respect to the pose of recipient 502 may dynamically change to be any angle between 0° and 360° as sound source 506 moves and/or as the pose of recipient 502 changes (e.g., as recipient 502 rotates or moves his or her head). While angle 802 is illustrated on a two-dimensional circle around recipient 502 in the illustration of FIG. 8, it will be understood that in certain implementations the angle may be associated with a three-dimensional sphere. Accordingly, while angle 802 may represent an azimuth angle with respect to recipient 502, an elevation angle may also be accounted in some implementations.

As shown, binaural hearing system 700 is shown to be worn by recipient 502, including hearing device 702-L at left ear 504-L, hearing device 702-R at right ear 504-R, and communication link 704 between hearing devices 702. Accordingly, system 100 (in this case implemented within binaural hearing system 700 and/or implemented independently by each of hearing devices 702) may be configured to dynamically identify angle 802 from where sound from sound source 506 originates, and, based on this identified angle 802, may determine whether and how various types of enhancements are to be activated and applied. Besides being highly dependent on individual characteristics of recipient 502 (e.g., an audiogram of recipient 502, loudness growth functions of recipient 502, the natural ability of recipient 502 to understand speech, etc.), the effectiveness of algorithms for localization and speech comprehension enhancement is also highly dependent on the listening situation, including the direction (e.g., angle 802) of speech and noise sources. Accordingly, activation and parameterization (i.e., setting particular localization parameters or speech comprehension parameters) of localization and/or speech enhancement algorithms may be performed based on angle 802 and/or other situation-specific characteristics that may be detected.

To illustrate, FIG. 9 shows an exemplary frequency-specific enhancement plan 900 ("plan 900") in which recipient 502 is assumed to be using a bimodal, binaural hearing system that includes a cochlear implant device at left ear 504-L and a hearing aid at right ear 504-R. As shown, plan 900 indicates different types of localization and speech comprehension enhancements to be applied to incoming frequency components at different frequency ranges for different exemplary angles 802. For example, plan 900 includes columns for sound source 506 to be located at an angle 802 of 0° (directly in front of recipient 502), at an angle of 90° (directly to the left of recipient 502, on the side with the cochlear implant device), at an angle of 180° (directly behind recipient 502), and at an angle of 270° (directly to the right of recipient 502, on the side with the hearing aid device). It will be understood that other specific angles may also be included in certain implementations of frequency-specific enhancement plans similar to plan 900, and that plan 900 may handle other angles 802 not explicitly shown in any suitable way. For example, such angles may be handled in a similar manner as the nearest angle that is accounted for by plan 900 (e.g., handling an angle 802 of 100° as indicated in the column for 90°, handling an angle 802 of 150° as indicated in the column for 180°, etc.). In other examples, such angles may be handled using a combination of the techniques indicated for the nearest angles accounted for by plan 900.

For each of the columns associated with angles 802, plan 900 shows a plurality of frequency ranges (shown in the "Frequency Range" column) associated with different types of enhancements (shown in the "Enhancement" column). These multiple frequency ranges associated with each type of enhancement represent an additional level of complexity over simpler, dual-frequency-range types of implementations that have been described above.

In certain examples, only two frequency ranges (e.g., a high frequency range and a low frequency range) separated by a particular crossover frequency may be employed. Specifically, a first frequency range (i.e., a low frequency range in this example) may include all the audible frequencies lower than a crossover frequency, while a second frequency range (i.e., a high frequency range in this example) may include all the audible frequencies greater than the crossover frequency. Frequencies that can be considered "audible frequencies" may vary from person to person and can range from about 20 Hz to about 20 kHz for certain individuals. Most audible frequency components that must be perceived to comprehend speech and otherwise perceive the world will be assumed for the following examples to be between 0 Hz and 8.0 kHz.

In a dual-frequency-range type of implementation, the single crossover frequency may be set (e.g., based on recipient characteristics, preferences, etc.) to be at a particular frequency (e.g., 900 Hz in one example). Accordingly, the low frequency range may include all frequency components up to the crossover frequency (e.g., 0 Hz to 900 Hz in this example), while the high frequency range may include all audible frequency components above the crossover frequency (e.g., 900 Hz to 8.0 kHz in this example). In some implementations, different frequency components may be associated with FFT bins or other types of predetermined frequency channels, which may be defined in any suitable manner. For example, one implementation of a hearing device may divide incoming audio signals into 16 different frequency channels. As such, the low frequency range may be associated with a certain subset of these channels (e.g., channels 1-5) while the high frequency range may be associated with another subset of these channels (e.g., channels 6-16).

The distribution of the channels and the selection of the crossover frequency may be performed in any suitable way, and may be customized to a specific recipient based on a fitting procedure. For example, the fitting procedure may involve determining an individual audiogram for a recipient and determining which ear is the stronger performing of the two. The crossover frequency may then be set to the highest frequency which allows functional hearing on the hearing aid side (the "acoustic ear") based on the performance difference between ears. Specifically, if the performance (e.g., speech understanding in noise) is poor in the acoustic ear, the crossover frequency may be decreased to allow more information to be transmitted (e.g., via CROS operations) to the cochlear implant device, since the cochlear implant device is the stronger ear capable of hearing a wider range of frequencies. Conversely, if the performance is good in the acoustic ear, the crossover frequency may be increased such that less information will be transmitted to the cochlear implant system via CROS operations.

Additionally, an individual mixing ratio may be determined for each ear based on how well each ear performs. For example, if the non-acoustic ear on the cochlear implant side performs well, the weight of the signal transmitted from the acoustic (hearing aid) ear will be relatively high. Conversely, if the non-acoustic ear on the cochlear implant side does not perform particularly well, the weight of the transmitted signal will be lower. The mixing ratio may also be determined based on the situation, and based in particular on the signal-to-noise ratio at each of the ears. If the signal-to-noise ratio is relatively high as the signal is transmitted via CROS operations, the weight given to the contralateral signal at the receiving side will be relatively great.

While dual-frequency-range type implementations may serve certain recipients well, other recipients may perform better with a multi-frequency-range type implementation including a plurality of crossover frequencies, such as shown in plan 900. Specifically, in these implementations, first and second frequency signals such as those described herein (e.g., frequency signals 414) may be included within a set of interleaved frequency signals that further includes a third frequency signal associated with a third frequency range, a fourth frequency signal associated with a fourth frequency range, and potentially additional frequency signals associated with additional respective frequency ranges. Here again, the first frequency range may include audible frequencies lower than one particular crossover frequency (a first crossover frequency) and the second frequency range may include audible frequencies greater than the particular crossover frequency. However, because of the inclusion of the additional frequency signals and respective frequency ranges, the second frequency range may be limited to be lower than a second crossover frequency. In turn, the third frequency range may include audible frequencies greater than the second crossover frequency and lower than a third crossover frequency; the fourth frequency range may include audible frequencies greater than the third crossover frequency and lower than a fourth crossover frequency; and so forth for however many frequency signals and frequency ranges might be included in a particular implementation (e.g., five frequency signals and frequency ranges in the example of plan 900).

As shown in FIG. 900, the types of enhancements assigned to each respective frequency signal associated with each respective frequency range may be interleaved so that the recipient can be facilitated in localization tasks and speech comprehension tasks throughout the whole audible frequency range. Specifically, the generating of an output frequency signal (e.g., analogous to frequency signal 416 if there were more than two frequency signals 414) may further include processing the third frequency signal together with the first frequency signal to apply the localization enhancement to the first and third frequency signals, processing the fourth frequency signal together with the second frequency signal to apply the speech comprehension enhancement to the second and fourth frequency signals, and so forth. As shown in plan 900, three disparate frequency ranges (i.e., 0 Hz-900 Hz, 1.8 kHz-3.0 kHz, and 4.5 kHz-8.0 kHz) are each associated with localization enhancements, while two interleaved frequency ranges filling in the gaps (i.e., 900 Hz-1.8 kHz and 3.0 kHz-4.5 kHz) are associated with speech comprehension enhancements. This interleaving may be beneficial particularly for recipients who are able to use localization cues at frequencies greater than a relatively low frequency such as 900 Hz (e.g., recipients who still have residual hearing above 900 Hz).

While dual-frequency-range type implementations have been described herein and a five-part multi-frequency-range type implementation is illustrated in FIG. 9, it will be understood that any suitable plurality of frequency ranges may be used as may serve a particular implementation. At the extreme, for example, every frequency component (e.g., every FFT bin, every channel, etc.) into which an audio signal is divided could be associated with its own frequency range, with all odd frequency components being associated with localization enhancements and all even frequency components being associated with speech comprehension enhancements (or vice versa).

As shown in plan 900, IABF operations ("IABF"), which will be understood to be combined with or replaced by other ILD/ITD enhancements or preservation techniques in certain examples, may be performed for all the frequency signals associated with frequency ranges assigned to localization enhancement, regardless of the angle of the sound source. However, IABF operations are not activated in frequency ranges assigned to speech comprehension enhancement, regardless of the angle of the sound source. Directional microphone tracking enhancements ("Directional mics") may be implemented whenever the sound source is detected to be located in front (0°) or behind (180°) the recipient, regardless of the frequency range or type of enhancement. However, directional microphone tracking enhancements may be disabled whenever the sound source is detected to be to the side of the recipient. In these situations, an appropriate type of CROS operation is applied to frequency signals associated with frequency ranges assigned to speech comprehension enhancements. For example, if the sound source is at 90° (on the cochlear implant side), a CROS operation to transmit the detected audio signal to the hearing aid device may be performed (assuming that the recipient has an ability to hear those frequencies in the acoustic ear, which may not be the case for certain high frequency ranges). As another example, if the sound source is at 270° (on the hearing aid side), a CROS operation to transmit the detected audio signal to the cochlear implant device may be performed.

In certain implementations, it may be desirable for ILD enhancements such as IABF operations and the like to be individually customized to specific recipients. For example, by determining with precision where a recipient perceives sound originating from (based on his or her localization ability) and how this compares to where the sound actually originates from, inaccuracies may be compensated for, at least in part, by properly configured hearing devices. As another example, the brains of certain recipients may have developed, over time, substitute localization strategies that rely less on ILD cues and more on other types of cues (e.g., the "sharpness" or "dullness" of a sound's character, as affected by head-shadow). For such recipients, it may be helpful to customize the degree to which ILD cues are enhanced (e.g., by customizing the size and shape of the end-fire directional polar pattern shown in FIG. 6, etc.) to help the recipients learn to rely on ILD cues provided by the system.

Determining individual recipient characteristics to allow for system customization in these ways may be performed in any suitable manner. For example, a control interface presented to the recipient by way of a mobile device or the like may be employed to determine what the recipient perceives. System 100 may then be configured to generate perception data based on user input provided by the recipient to the control interface. For example, the perception data may be representative of audibility and loudness perceived by the recipient, an ability of the recipient to localize sound, an ability of the recipient to comprehend speech presented to the recipient, and/or any other suitable characteristic associated with the recipient and/or his or her perception of sound. System 100 may process the frequency signals (e.g., frequency signals 414) to apply the localization and speech comprehension enhancements based on the perception data.

Figure 10:
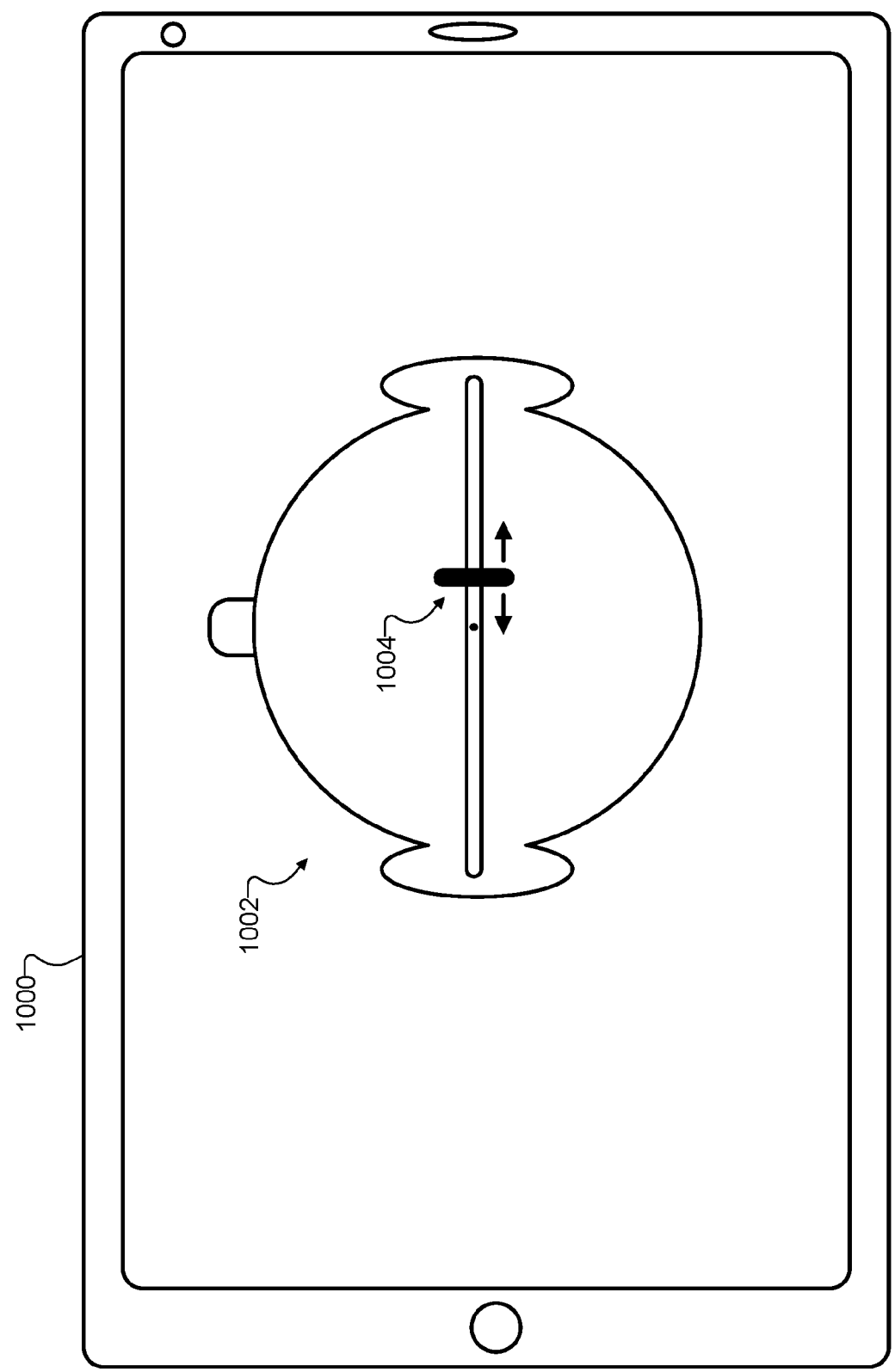
FIG. 10 illustrates an exemplary control interface by way of which a recipient provides perception data representative of audibility or loudness perceived by the recipient, or an ability of the recipient to localize sound and/or comprehend speech according to principles described herein.

To illustrate, FIG. 10 shows an exemplary control interface by way of which a recipient provides perception data representative of audibility or loudness perceived by the recipient, or an ability of the recipient to localize sound and/or comprehend speech. Specifically, FIG. 10 shows a device 1000 (e.g., a smartphone, a tablet device, a laptop or other personal computer, a dedicated device specific to the hearing system, a fitting tool used by a clinician, etc.) that presents a control interface 1002 that allows for specific information for a particular recipient to be input. Control interface 1002 may include any suitable type of graphical or text-based user interface to allow data to be input for the particular recipient. In some examples, control interface 1002 may be configured to present a sound to the recipient (e.g., via headphones worn by the recipient, via loudspeakers coupled to device 1000, etc.) and to prompt the recipient (or a clinician administering a test to the recipient) to indicate what the recipient perceives. For instance, as shown in the example of FIG. 10, after a sound has been presented, the recipient may be asked to slide a slider tool 1004 to a particular point between a representation of the left and right ears of the recipient to indicate an ILO that the recipient perceives (i.e., how much louder the sound is perceived in one ear versus the other).

As mentioned above, the systems and methods described herein may be particularly beneficial for recipients of bimodal hearing systems, such as a hearing system that includes a hearing aid device (e.g., at the right ear, such as in the example described in connection with FIG. 9) and a cochlear implant device (e.g., at the left ear, such as in the example of FIG. 9), One reason for this is that the cochlear implant may provide stimulation at a wide range of frequencies (making the cochlear implant side the "strong" ear), while the hearing aid may be limited to providing stimulation at whatever frequencies the recipient is able to naturally hear (which may be a much more limited range, especially at the high end, thus making the hearing aid side the "weak" ear). Accordingly, a situation may commonly be encountered by such bimodal recipients where speech originates from the right side (i.e., at about 270° on the weak side with the hearing aid). Without being able to perceive high frequencies included in the speech originating from that side, the recipient may not be able to comprehend the speech well unless he or she turn his or her head to point his or her left ("strong") ear toward the speaker. Alternatively, a conventional CROS operation to automatically send the audio captured at the hearing aid to be perceived in the left ear may be used to avoid the head rotation, but, as described above, conventional CROS operations may seriously degrade the localization ability of the recipient, making that option problematic as well.

The most beneficial solution to this situation, then, involves the systems and methods described herein for frequency-specific localization and speech comprehension enhancement. Specifically, a CROS operation may send certain frequencies integral to speech (e.g., frequencies above a crossover frequency determined in any of the ways described herein) from the hearing aid device to the cochlear implant device. However, other frequencies (e.g., lower frequencies that are not as important for comprehending speech) may not be transmitted in this way. Instead, localization enhancements such as IABF or the like may be performed for signals at these frequencies to allow the recipient to retain his or her ability to localize sounds even while enjoying the benefits of enhanced speech comprehension provided by the CROS operation.

Figure 11:
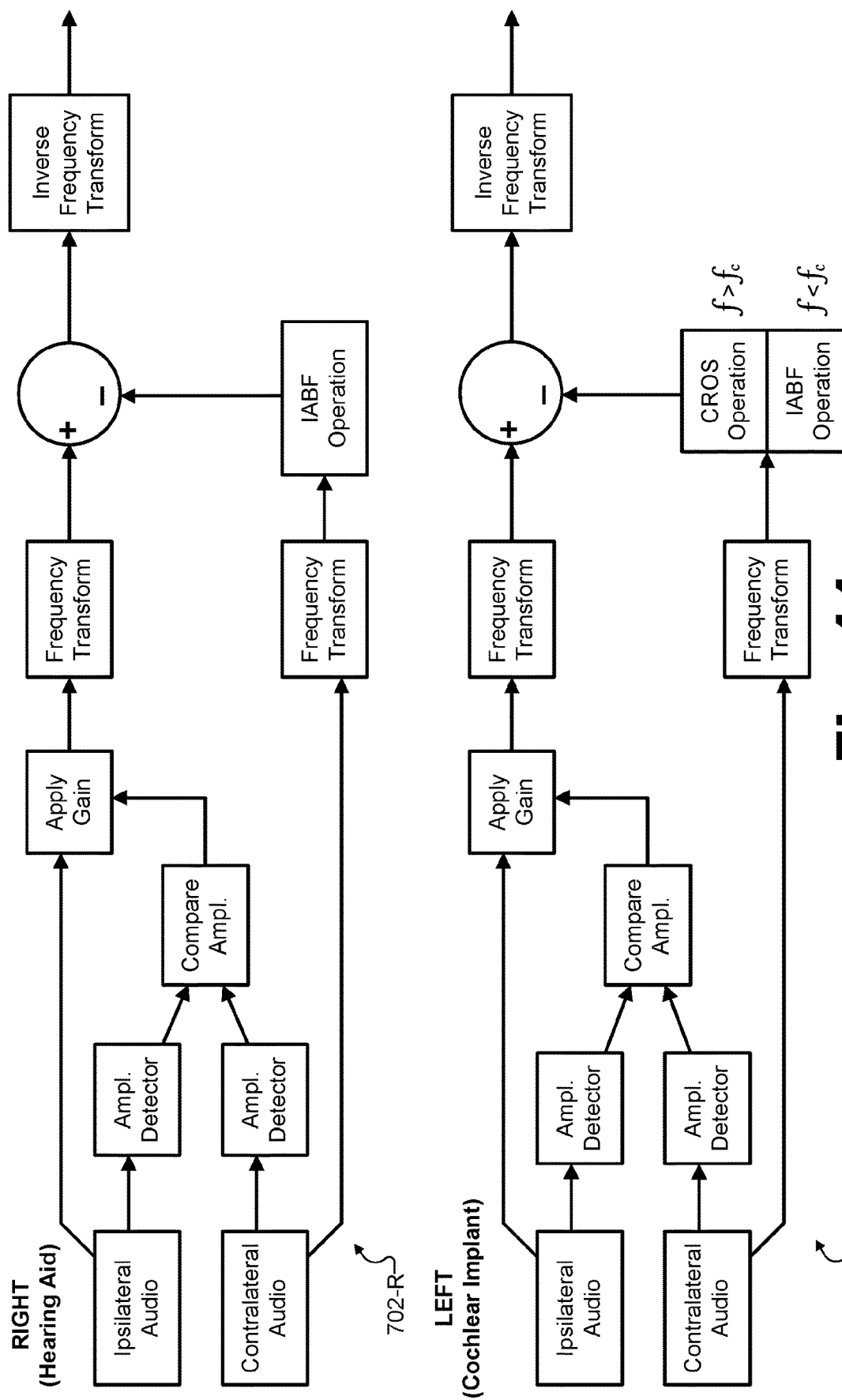
FIG. 11 illustrates a block diagram of an exemplary implementation of a bimodal hearing system for frequency-specific localization and speech comprehension enhancement according to principles described herein.

To illustrate, FIG. 11 shows a block diagram of an exemplary implementation of an implementation of bimodal hearing system 700 that includes hearing device 702-R implemented on the right side by a hearing aid device such as hearing aid device 200-B, and hearing device 702-L implemented on the left side by a cochlear implant device such as cochlear implant device 200-A. As shown, each hearing device 702 has access to both the ipsilateral signal (i.e., detected by an audio input device included within that hearing device) and the contralateral signal (i.e., received by way of communication link 704, not explicitly shown in FIG. 11).

Prior to transforming audio signals into frequency signals, FIG. 11 shows that respective operations are performed to couple the gain that is to be applied to each ipsilateral signal. Specifically, system 100 may implement a binaural gain coupling between the cochlear implant and hearing aid devices by applying a same gain: 1) by the hearing aid device to the audio signal as received at the hearing aid device (i.e., to the ipsilateral signal received by the hearing aid device), and 2) by the cochlear implant device to the audio signal as received at the cochlear implant device (i.e., to the ipsilateral signal received by the cochlear implant device). This binaural gain coupling may be used to preserve ILD cues with respect to any suitable type of gain processing as may serve a particular implementation. For example, the binaural gain coupling may be performed for automatic gain control ("AGC") processing, noise cancelation processing, wind cancelation processing, reverberation cancelation processing, impulse cancelation processing, or any other suitable type of gain processing. By coupling the gain invoked by each hearing device, ILD cues may be preserved so as to not be diminished by independent applications of gain at each hearing device 702. In this way, the ILD cues may be preserved such that they may be enhanced by localization enhancements such as IABF operations or the like. In some examples, a difference in gains may be maintained or added even within the binaural gain coupling so as to account for different amounts of hearing loss in each ear.

As shown, the gain coupling is performed at each hearing device 702 by receiving both ipsilateral and contralateral signals, determining the respective amplitudes of each of these signals ("Ampl. Detector"), comparing the respective amplitudes of each of these signals to determine what gain is to be applied on both sides ("Compare Ampl."), and then applying the determined gain to the respective ipsilateral signal ("Apply Gain"). In this way, even though each hearing device is operating independently, the same gain should be applied to the ipsilateral signal at each side, thereby preserving the level difference of the signal from one side to the other (i.e., the ILD cue).

Once these gain coupling operations have been performed, FIG. 11 shows that each hearing device 702 performs the operations described above to implement frequency-specific localization and speech comprehension enhancement. Specifically, each hearing device 702 transforms the ipsilateral and contralateral audio signals into frequency signals ("Frequency Transform") and performs spatial enhancement operations on the frequency signals. For the hearing aid (on the right side where speech is originating), these spatial enhancement operations may include only an IABF operation or other similar localization enhancement operations ("IABF Operation"). For the cochlear implant (on the left side opposite to where the speech is originating), however, the spatial enhancement operations may include both the IABF localization enhancement operation for frequency components less than the crossover frequency ("$f<f_c$"), as well as a CROS operation ("CROS Operation") for frequency components greater than the crossover frequency ("$f<f_c$"), such that the speech captured contralaterally will be mixed in at a greater volume to facilitate speech comprehension. Frequency signals from both the ipsilateral and contralateral sides are then shown to be mixed and inversely transformed back into audio signals having the benefits that have been described.

Figure 12:
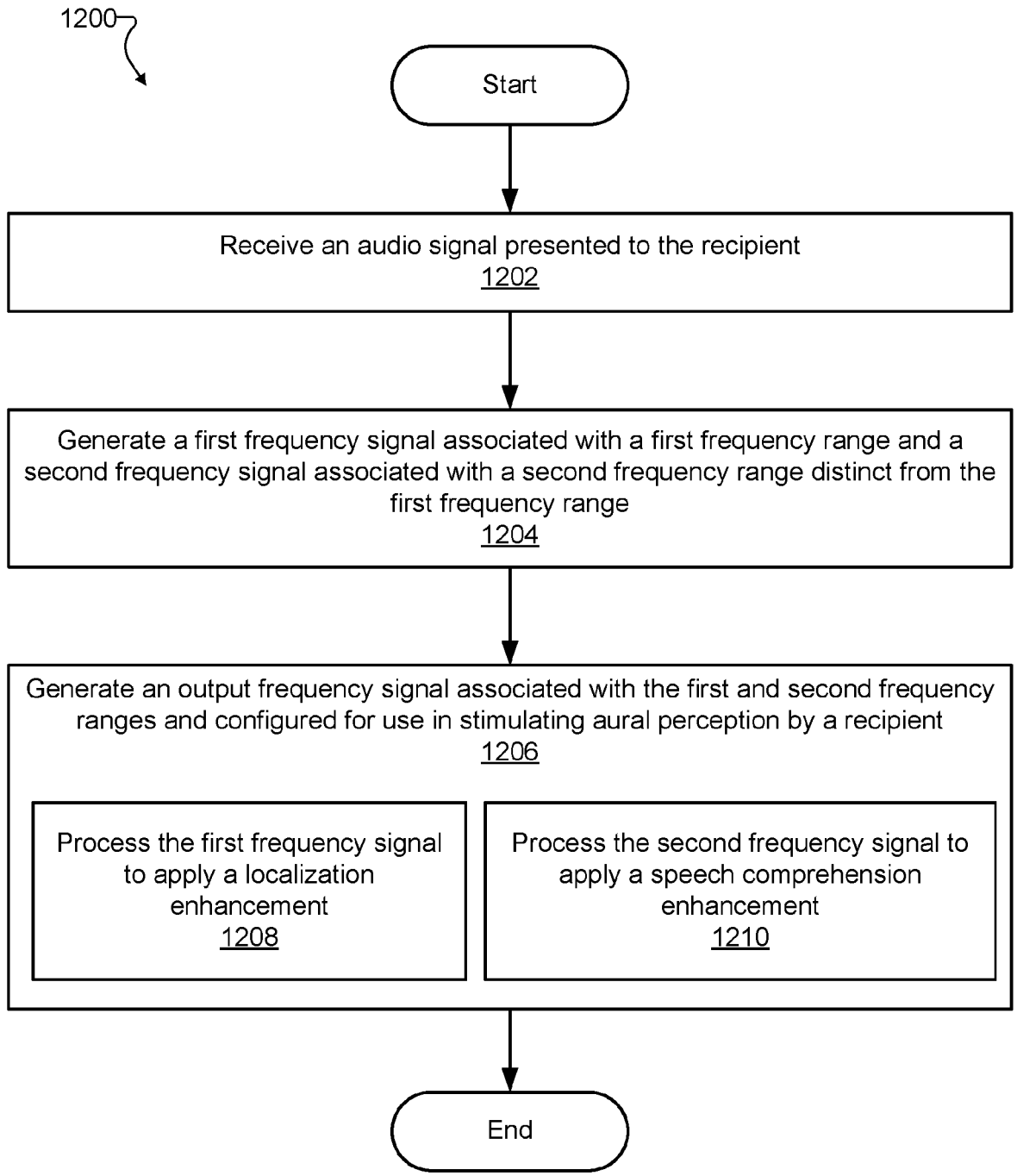
FIG. 12 illustrates an exemplary method for frequency-specific localization and speech comprehension enhancement according to principles described herein.

FIG. 12 illustrates an exemplary method 1200 for frequency-specific localization and speech comprehension enhancement. One or more of the operations shown in FIG. 12 may be performed by a spatial enhancement system such as system 100 and/or any implementation thereof. While FIG. 12 illustrates exemplary operations according to one embodiment, other embodiments may omit, add to, reorder, and/or modify any of the operations shown in FIG. 12. In some examples, some or all of the operations shown in FIG. 12 may be performed by a sound processor (e.g., one of sound processors 204) while another sound processor (e.g., included in a contralateral hearing device included in the same hearing system) performs similar operations in parallel.

In operation 1202, a spatial enhancement system associated with a hearing device used by a recipient may receive an audio signal presented to the recipient. Operation 1202 may be performed in any of the ways described herein.

In operation 1204, the spatial enhancement system may generate a first frequency signal and a second frequency signal based on the audio signal. For example, the first frequency signal may include a portion of the audio signal associated with a first frequency range, while the second frequency signal may include a portion of the audio signal associated with a second frequency range. The second frequency range may be distinct from the first frequency range. Operation 1204 may be performed in any of the ways described herein.

In operation 1206, the spatial enhancement system may generate an output frequency signal based on the first and second frequency signals generated in operation 1204. For example, the output frequency signal may be associated with the first and second frequency ranges and may be configured for use by the hearing device in stimulating aural perception by the recipient. Operation 1206 may be performed in any of the ways described herein. For instance, the generating of the output frequency signal in operation 1206 may be performed by way of sub-operations 1208 and 1210, as well as any other sub-operations as may serve a particular implementation.

In sub-operation 1208, the spatial enhancement system may process the first frequency signal to apply a localization enhancement. In sub-operation 1210, the spatial enhancement system may process the second frequency signal to apply a speech comprehension enhancement. In some examples, the speech comprehension enhancement is different than the localization enhancement. Sub-operations 1208 and 1210 may be performed sequentially in any order or in parallel with one another and/or with other operations shown in method 1200.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions; and
a processor communicatively coupled to the memory and configured to execute the instructions to:

receive an audio signal presented to a recipient of a hearing device associated with a first ear of the recipient, the first ear located opposite a second ear of the recipient;

generate, based on the audio signal, a first frequency signal and a second frequency signal, the first frequency signal including a portion of the audio signal associated with a first frequency range, and the second frequency signal including a portion of the audio signal associated with a second frequency range distinct from the first frequency range; and generate, based on the first and second frequency signals, an output frequency signal associated with the first and second frequency ranges and configured for use by the hearing device in stimulating aural perception by the recipient, the generating of the output frequency signal including:

processing the first frequency signal to apply a localization enhancement, and processing the second frequency signal to apply a speech comprehension enhancement that is different than the localization enhancement, wherein the processing of the second frequency signal includes performing a contralateral routing of signal ("CROS") operation with respect to the second frequency signal to amplify, ipsilaterally at the first ear, an aspect of the audio signal that is received contralaterally at the second ear.

2. The system of claim 1, wherein the processing of the first frequency signal to apply the localization enhancement includes performing an interaural beamforming operation with respect to the first frequency signal to spatially filter the first frequency signal according to an end-fire directional polar pattern distinct from a polar pattern of the first frequency signal as generated based on the received audio signal.

3. The system of claim 1, wherein the processing of the first frequency signal to apply the localization enhancement includes processing:

a first version of the first frequency signal that has been spatially filtered according to an end-fire directional polar pattern, and a second version of the first frequency signal that has not been spatially filtered.

4. The system of claim 1, wherein:

the processing of the first frequency signal to apply the localization enhancement includes at least one of:

performing a localization enhancement operation in accordance with a set of localization parameters, and dynamically adjusting, during the performing of the localization enhancement operation in accordance with the set of localization parameters, at least one localization parameter in the set of localization parameters; and the processing of the second frequency signal to apply the speech comprehension enhancement further includes at least one of:

performing a speech comprehension enhancement operation in accordance with a set of speech comprehension parameters, or dynamically adjusting, during the performing of the speech comprehension enhancement operation in accordance with the set of speech comprehension parameters, at least one speech comprehension parameter in the set of speech comprehension parameters.

5. The system of claim 1, wherein:

the first frequency range includes all the audible frequencies lower than a crossover frequency;

the second frequency range includes all the audible frequencies greater than the crossover frequency.

6. The system of claim 1, wherein:

the first and second frequency signals are included within a set of interleaved frequency signals that further includes a third frequency signal associated with a third frequency range and a fourth frequency signal associated with a fourth frequency range;

the first frequency range includes audible frequencies lower than a first crossover frequency;

the second frequency range includes audible frequencies greater than the first crossover frequency and lower than a second crossover frequency;

the third frequency range includes audible frequencies greater than the second crossover frequency and lower than a third crossover frequency;

the fourth frequency range includes audible frequencies greater than the third crossover frequency; and the generating of the output frequency signal further includes:

processing the third frequency signal together with the first frequency signal to apply the localization enhancement to the first and third frequency signals, and processing the fourth frequency signal together with the second frequency signal to apply the speech comprehension enhancement to the second and fourth frequency signals.

7. The system of claim 1, wherein:

the memory and the processor are implemented by the hearing device; and the hearing device is a first hearing device that is included in a binaural hearing system that also includes a second hearing device comprising:

a second memory storing additional instructions, and a second processor communicatively coupled to the memory and configured to execute the additional instructions to perform operations analogous to the receiving of the audio signal, the generating of the first and second frequency signals, and the generating of the output frequency signal that are performed by the processor implemented by the first hearing device.

8. The system of claim 7, wherein the binaural hearing system is a bimodal hearing system in which:

the first hearing device is implemented by a first type of hearing device selected from a cochlear implant device, a hearing aid device, and a hybrid stimulation device; and the second hearing device is implemented by a second type of hearing device that is also selected from the cochlear implant device, the hearing aid device, and the hybrid stimulation device, and that is different from the first type of hearing device.

9. The system of claim 7, wherein the binaural hearing system is a binaural cochlear implant system in which the first and second hearing devices are each implemented as cochlear implant devices including respective cochlear implants and sound processors.

10. The system of claim 7, wherein the binaural hearing system is a binaural hearing aid system in which the first and second hearing devices are each implemented as hearing aid devices.

11. The system of claim 7, wherein the binaural hearing system is a binaural hybrid stimulation system in which the first and second hearing devices are each implemented as hybrid stimulation devices including respective cochlear implants and sound processors.

12. The system of claim 7, wherein the processor is further configured to execute the instructions to implement a binaural gain coupling between the first and second hearing devices, the binaural gain coupling implemented by applying a same gain
by the first hearing device to the audio signal as received at the first hearing device, and
by the second hearing device to the audio signal as received at the second hearing device.

13. The system of claim 1, wherein:
the processor is further configured to execute the instructions to generate, based on user input provided by the recipient to a control interface communicatively coupled to the processor, perception data representative of at least one of:
audibility and loudness perceived by the recipient,
an ability of the recipient to localize sound, or
an ability of the recipient to comprehend speech presented to the recipient; and
the processing of the first frequency signal and the processing of the second frequency signal are each performed based on the perception data.

14. A bimodal hearing system comprising:
a cochlear implant device associated with a first ear of a recipient of the bimodal hearing system and configured to:
receive, at the first ear, an audio signal presented to the recipient,
generate, based on the audio signal as received at the first ear, a first low-frequency signal and a first high-frequency signal, the first low-frequency signal including a portion of the audio signal associated with a low frequency range including audible frequencies lower than a crossover frequency, and the first high-frequency signal including a portion of the audio signal associated with a high frequency range including audible frequencies greater than the crossover frequency, and
generate, based on the first low-frequency and high-frequency signals, a first output frequency signal associated with the low and high frequency ranges and configured for use by the cochlear implant device in stimulating aural perception by the recipient at the first ear, the generating of the first output frequency signal including
processing the first low-frequency signal to apply a localization enhancement, and
processing the first high-frequency signal to apply a speech comprehension enhancement that is different than the localization enhancement; and
a hearing aid device associated with a second ear of the recipient opposite the first ear, the hearing aid device configured to:
receive, at the second ear, the audio signal presented to the recipient,
generate, based on the audio signal as received at the second ear, a second low-frequency signal and a second high-frequency signal, the second low-frequency signal including the portion of the audio signal associated with the low frequency range, and the second high-frequency signal including the portion of the audio signal associated with the high frequency range, and
generate, based on the second low-frequency and high-frequency signals, a second output frequency signal associated with the low and high frequency ranges and configured for use by the hearing aid device in stimulating aural perception by the recipient at the second ear, the generating of the second output frequency signal including
processing the second low-frequency signal to apply the localization enhancement, and
processing the second high-frequency signal to apply the speech comprehension enhancement.

15. The system of claim 14, wherein the processing of the first and second low-frequency signals to apply the localization enhancement includes performing an interaural beamforming operation with respect to each of the first and second low-frequency signals to spatially filter the respective first and second low-frequency signals according to an end-fire directional polar pattern distinct from respective polar patterns of the first and second low-frequency signals as generated based on the received audio signal.

16. The system of claim 14, wherein the processing of the first and second high-frequency signals to apply the speech comprehension enhancement includes performing a contralateral routing of signal ("CROS") operation with respect to each of the first and second high-frequency signals to amplify, ipsilaterally at each respective ear, an aspect of the audio signal that is received contralaterally at each opposite ear.

17. The system of claim 14, wherein the processing of the first frequency signal to apply the localization enhancement includes processing:
a first version of the first frequency signal that has been spatially filtered according to an end-fire directional polar pattern, and
a second version of the first frequency signal that has not been spatially filtered.

18. The system of claim 14, wherein:
the processing of the first and second low-frequency signals to apply the localization enhancement includes at least one of:
performing a localization enhancement operation in accordance with a set of localization parameters, or
dynamically adjusting, during the performing of the localization enhancement operation in accordance with the set of localization parameters, at least one localization parameter in the set of localization parameters; and
the processing of the first and second high-frequency signals to apply the speech comprehension enhancement includes at least one of:
performing a speech comprehension enhancement operation in accordance with a set of speech comprehension parameters, and
dynamically adjusting, during the performing of the speech comprehension enhancement operation in accordance with the set of speech comprehension parameters, at least one speech comprehension parameter in the set of speech comprehension parameters.

19. A method comprising:
receiving, by a spatial enhancement system associated with a hearing device associated with a first ear of a recipient, an audio signal presented to the recipient, the first ear located opposite a second ear of the recipient;
generating, by the spatial enhancement system and based on the audio signal, a first frequency signal and a second frequency signal, the first frequency signal including a portion of the audio signal associated with a first frequency range, and the second frequency signal including a portion of the audio signal associated with a second frequency range distinct from the first frequency range; and generating, by the spatial enhancement system and based on the first and second frequency signals, an output frequency signal associated with the first and second frequency ranges and configured for use by the hearing device in stimulating aural perception by the recipient, the generating of the output frequency signal including:

processing the first frequency signal to apply a localization enhancement, and processing the second frequency signal to apply a speech comprehension enhancement that is different than the localization enhancement, wherein the processing of the second frequency signal includes performing a contralateral routing of signal ("CROS") operation with respect to the second frequency signal to amplify, ipsilaterally at the first ear, an aspect of the audio signal that is received contralaterally at the second ear.

20. The method of claim 19, wherein the processing of the first frequency signal to apply the localization enhancement includes performing an interaural beamforming operation with respect to the first frequency signal to spatially filter the first frequency signal according to an end-fire directional polar pattern distinct from a polar pattern of the first frequency signal as generated based on the received audio signal.

* * * * *